United States Patent [19]
Mitjans et al.

[11] Patent Number: 5,985,278
[45] Date of Patent: Nov. 16, 1999

[54] ANTI-αV-INTEGRIN MONOCLONAL ANTIBODY

[75] Inventors: Francesc Mitjans, Igualada; Jaume Piulats; Elisabet Rosell, both of Barcelona; Jaume Adan, Mataro, all of Spain; Simon Goodman, Darmstadt; Diane Hahn, Otzberg, both of Germany

[73] Assignee: Merck Patent Gesellschaft mit Beschrankter Haftung, Germany

[21] Appl. No.: 08/574,699

[22] Filed: Dec. 19, 1995

[30] Foreign Application Priority Data

Dec. 20, 1994 [EP] European Pat. Off. ............. 94120165

[51] Int. Cl.$^6$ ................ A61K 39/395; C07K 16/28; C12N 15/13; C12N 5/12
[52] U.S. Cl. .................... 424/143.1; 424/130.1; 424/133.1; 424/138.1; 424/141.1; 424/152.1; 424/172.1; 435/70.21; 435/330; 435/326; 435/332; 435/346; 435/452; 530/387.1; 530/387.3; 530/387.7; 530/388.2; 530/388.22; 530/388.8; 536/23.53
[58] Field of Search ............... 424/130.1, 133.1, 424/138.1, 143.1; 530/387.1, 388.2; 435/70.21, 326, 346; 536/23.53

[56] References Cited

FOREIGN PATENT DOCUMENTS

WO-93-20229  10/1993  WIPO.
WO-95-25543   9/1995  WIPO.

OTHER PUBLICATIONS

Osband et. al Immunol. Today 11:193–195 (1990).
Dermer Biotechnology 12:320 (1994).
Dillman J Clin. Oncol. 12:1497–1515 (1994).
Lehmann et al., Cancer Research 54:2102–2107 (1994).
Cheresh et al., J. Biol. Chem. 262:17703–17711 (1987).
Mitjans et al., J. Cell Sci. 108:2825–2838 (1995).
Marshall et al., J. Cell Sci. 108:1227–1238 (1995).

*Primary Examiner*—Christina Y. Chan
*Assistant Examiner*—Phillip Gambel
*Attorney, Agent, or Firm*—Millen, White, Zelano, & Branigan, P.C.

[57] ABSTRACT

The invention relates to a novel monoclonal antibody, a hybridoma cell line producing said antibody, DNA sequences coding for said antibody, and amino acid sequences. The monoclonal antibody, a preferred embodiment of which is named 17E6, has the following properties:

reacting only with the αV-chain of human αV-integrins, blocking the attachment to the integrin substrate of the αV-integrin bearing cell, triggering reversal of established cell matrix interaction caused by αV-integrins, blocking tumor development, and showing no cytotoxic activity.

23 Claims, 19 Drawing Sheets

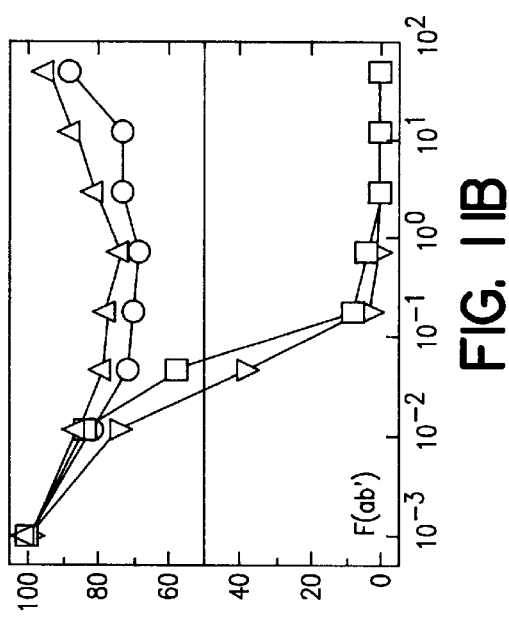
FIG. 11A
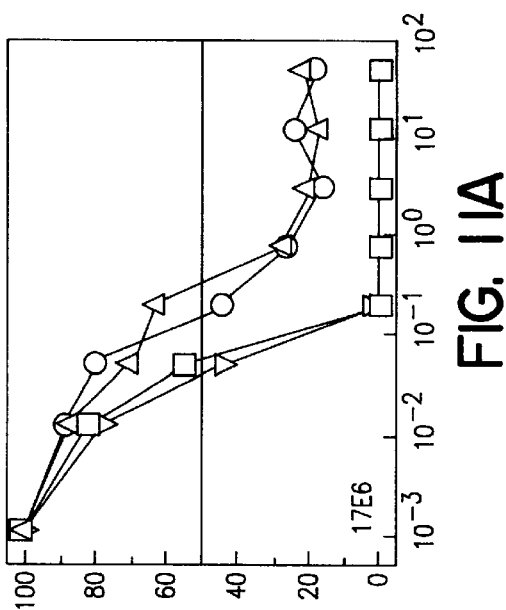
FIG. 11C
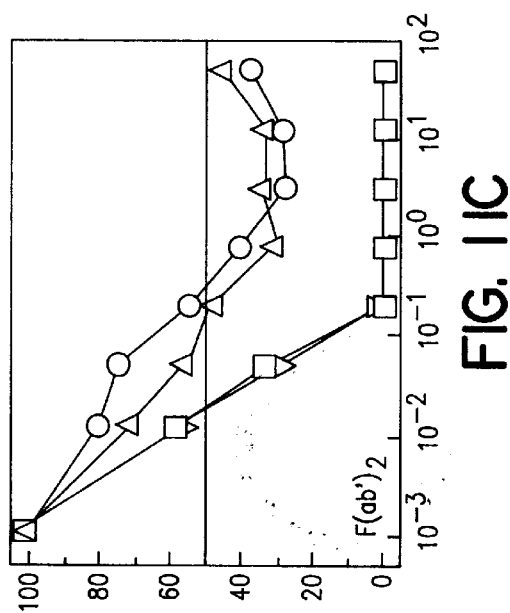
FIG. 11B
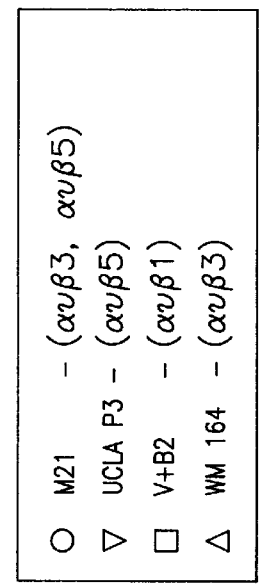

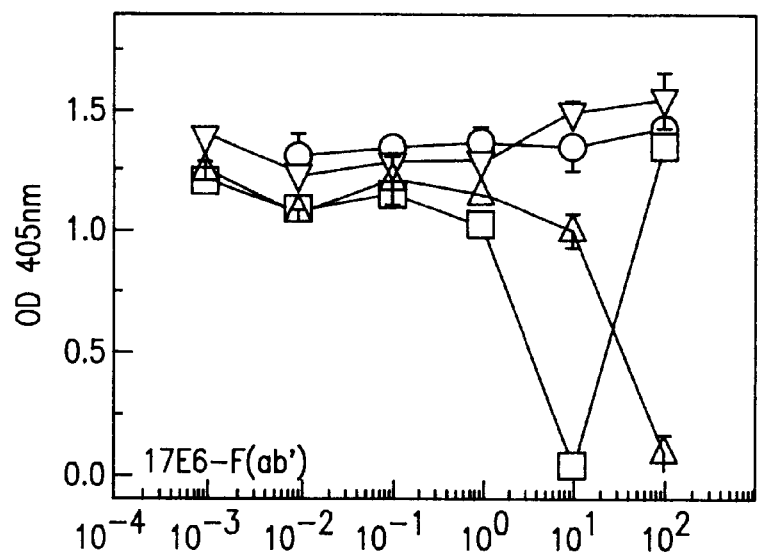
FIG. 12A
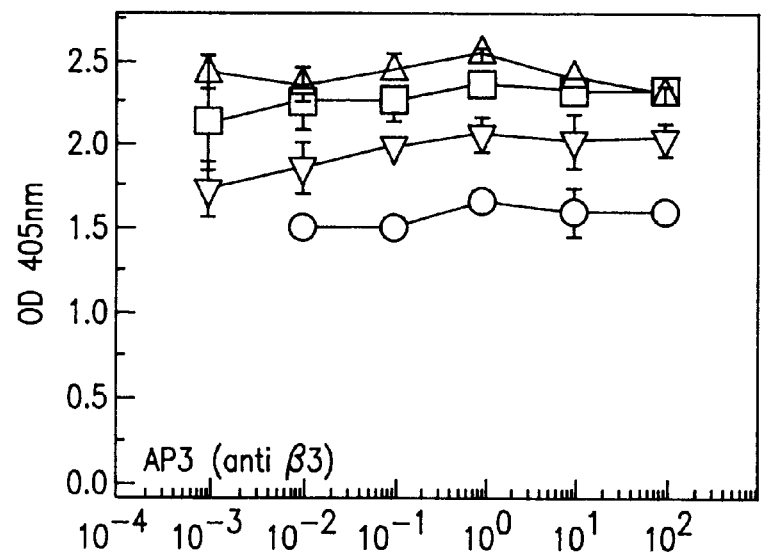
FIG. 12B
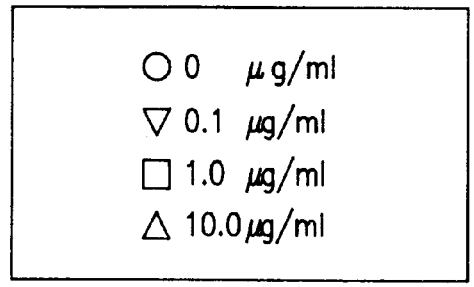

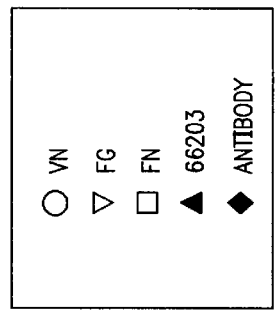
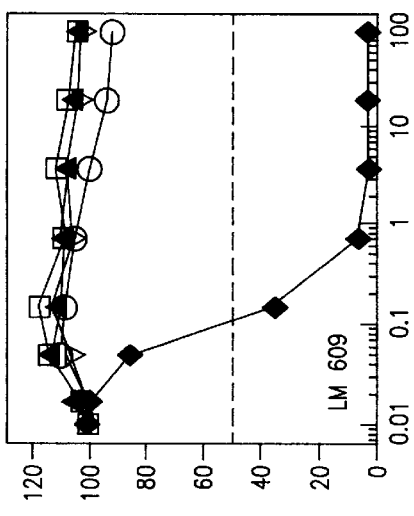
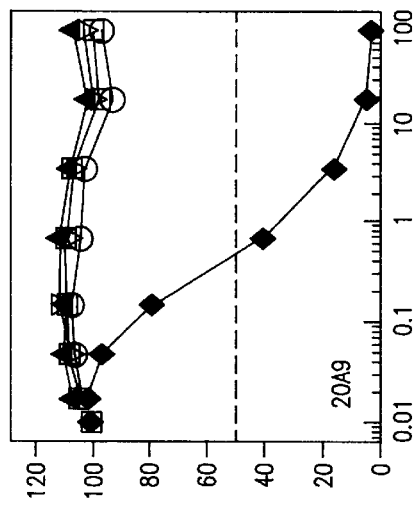
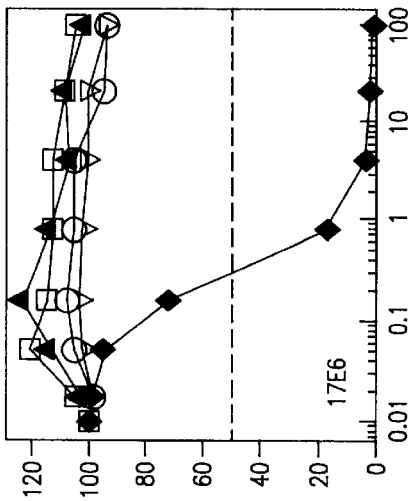
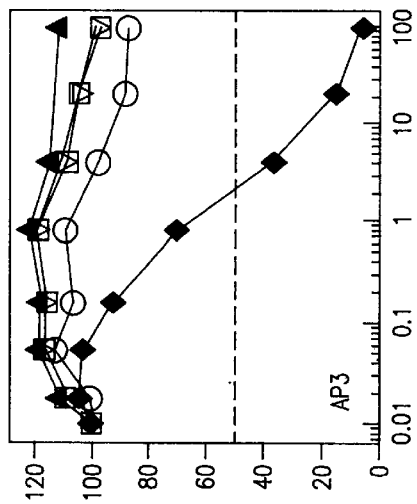

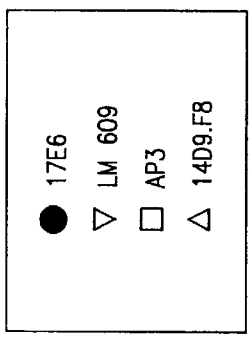
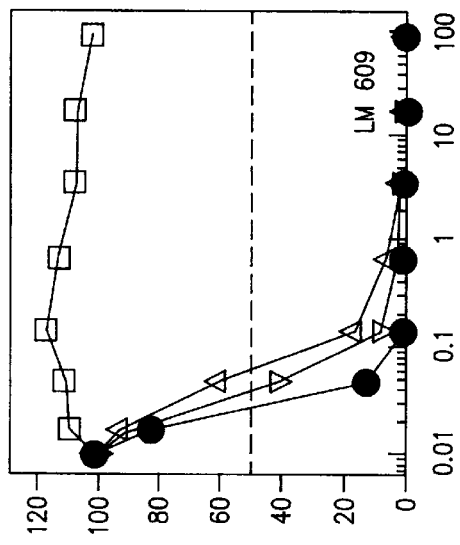
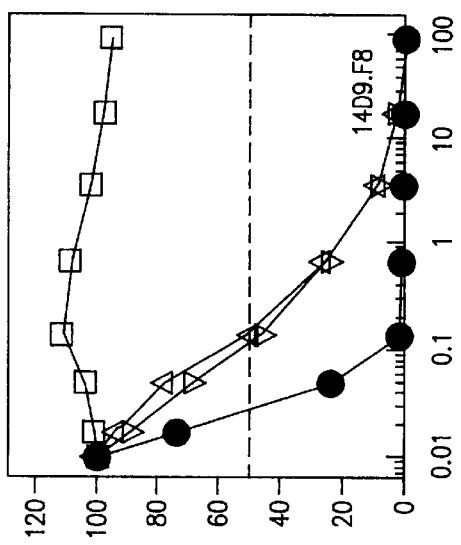
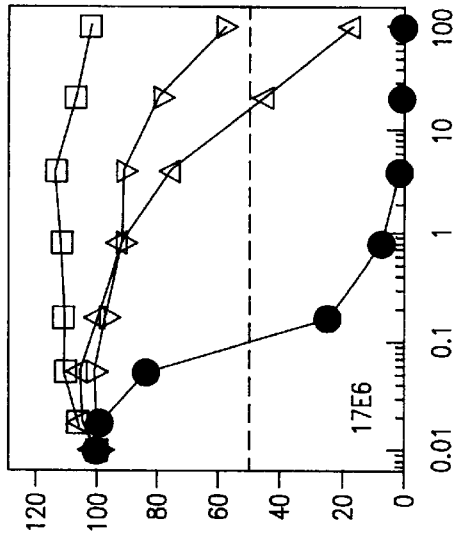
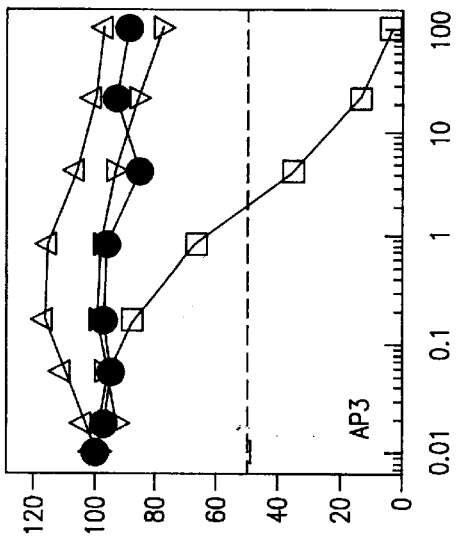

```
Leader
ATG GTG TCC TCA GCT CAG TTC CTT GGT CTC CTG TTG
Met Val Ser Ser Ala Gln Phe Leu Gly Leu Leu Leu 1   2   3   4
                                    FR1
CTC TGT TTT CAA GTT ACC AGA TGT GAT ATC CAG ATG
Leu Cys Phe Gln Val Thr Arg Cys Asp Ile Gln Met 5   6   7   8   9   10  11  12  13  14  15  16

ACA CAG ACT ACA TCC TCC CTG TCT GCC TCT CTG GGA
Thr Gln Thr Thr Ser Ser Leu Ser Ala Ser Leu Gly 17  18  19  20  21  22  23  24  25  26  27  28
                            CDR1
GAC AGA GTC ATC ATC AGT TGC AGG GCA AGT CAG GAC
Asp Arg Val Ile Ile Ser Cys Arg Ala Ser Gln Asp 29  30  31
                     FR2
ATT AGC AAT TAT TTA AGC TGG TAT CAA CAG AAG CCA
Ile Ser Asn Tyr Leu Ser Trp Tyr Gln Gln Lys Pro

CDR2
GAT GGA ACT GTT AAA CTC CTG ATC TTC TAC ACA TCA
Asp Gly Thr Val Lys Leu Leu Ile Phe Tyr Thr Ser

FR3
AAA TTA CAC TCA GGA GTC CCA TCA AGA TTC AGT GGC
Lys Leu His Ser Gly Val Pro Ser Arg Phe Ser Gly

AGT GGG TCT GGA ACA GAT TAT TCT CTC ACC ATT AGT
Ser Gly Ser Gly Thr Asp Tyr Ser Leu Thr Ile Ser

AAC CTG GAC CAA GAA GAT ATT GCC ACT TAC TTT TGC
Asn Leu Asp Gln Glu Asp Ile Ala Thr Tyr Phe Cys

CDR3                                FR4
CAA CAG GGT AAT ACG TTT CCG TAC ACG TTC GGA GGG
Gln Gln Gly Asn Thr Phe Pro Tyr Thr Phe Gly Gly

GGG ACA AAG GTG GAA ATG AGA
Gly Thr Lys Val Glu Met Arg
```

FIG. 17A

```
Leader
ATG  GGA  TGG  AGC  TGG  GTC  TTT  ATC  TTC  CTG  TTT  TCA
Met  Gly  Trp  Ser  Trp  Val  Phe  Ile  Phe  Leu  Phe  Ser FR1
GTA  ACT  GCA  GGT  GTC  CAC  TCC  CAG  GTC  CAG  CTT  CAG
Val  Thr  Ala  Gly  Val  His  Ser  Gln  Val  Gln  Leu  Gln CAG  TCT  GGG  GCT  GAA  CTG  GCA  GAG  CCT  GGG  GCC  TCA
Gln  Ser  Gly  Ala  Glu  Leu  Ala  Glu  Pro  Gly  Ala  Ser GTG  AAG  ATG  TCC  TGC  AAG  GCT  TCT  GGC  TAC  ACC  TTT
Val  Lys  Met  Ser  Cys  Lys  Ala  Ser  Gly  Tyr  Thr  Phe CDR1                      FR2
ATG  AGT  TTC  TGG  ATG  CAC  TGG  GTA  AAA  CAG  AGG  CCT
Ser  Ser  Phe  Trp  Met  His  Trp  Val  Lys  Gln  Arg  Pro CDR2
GGA  CAG  GGT  CTG  GAA  TGG  ATT  GGA  TAC  ATT  AAT  CCT
Gly  Gln  Gly  Leu  Glu  Trp  Ile  Gly  Tyr  Ile  Asn  Pro AGA  TCT  GGT  TAT  ACT  GAG  TGT  AAT  GAG  ATA  TTC  AGG
Arg  Ser  Gly  Tyr  Thr  Glu  Cys  Asn  Glu  Ile  Phe  Arg FR3
GAC  AAG  GCC  ACA  ATG  ACT  GCA  GAC  ACC  TCC  TCC  AGC
Asp  Lys  Ala  Thr  Met  Thr  Ala  Asp  Thr  Ser  Ser  Ser ACA  GCC  TAC  ATG  CAA  CTG  AGT  GGT  CTG  ACA  TCT  GAG
Thr  Ala  Tyr  Met  Gln  Leu  Ser  Gly  Leu  Thr  Ser  Glu CDR3
GAC  TCT  GCA  GTC  TAT  TAC  TGT  GCA  AGT  TTT  CTG  GGA
Asp  Ser  Ala  Val  Tyr  Tyr  Cys  Ala  Ser  Phe  Leu  Gly FR4
CGA  GGG  GCT  ATG  GAC  TAC  TGG  GGT  CAA  GGA  ACC  TCA
Arg  Gly  Ala  Met  Asp  Tyr  Trp  Gly  Gln  Gly  Thr  Ser GTC  ACC  GTC  TCC  TCA
Val  Thr  Val  Ser  Ser
```

FIG. 17B

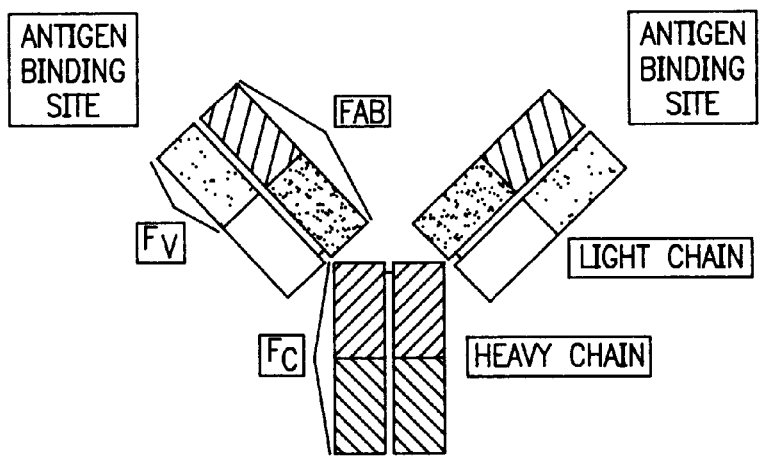
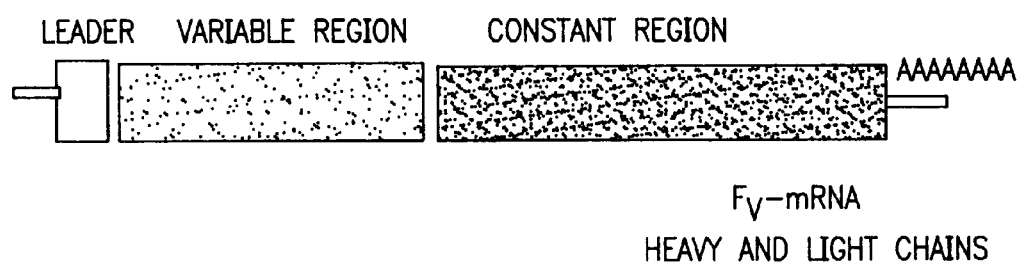
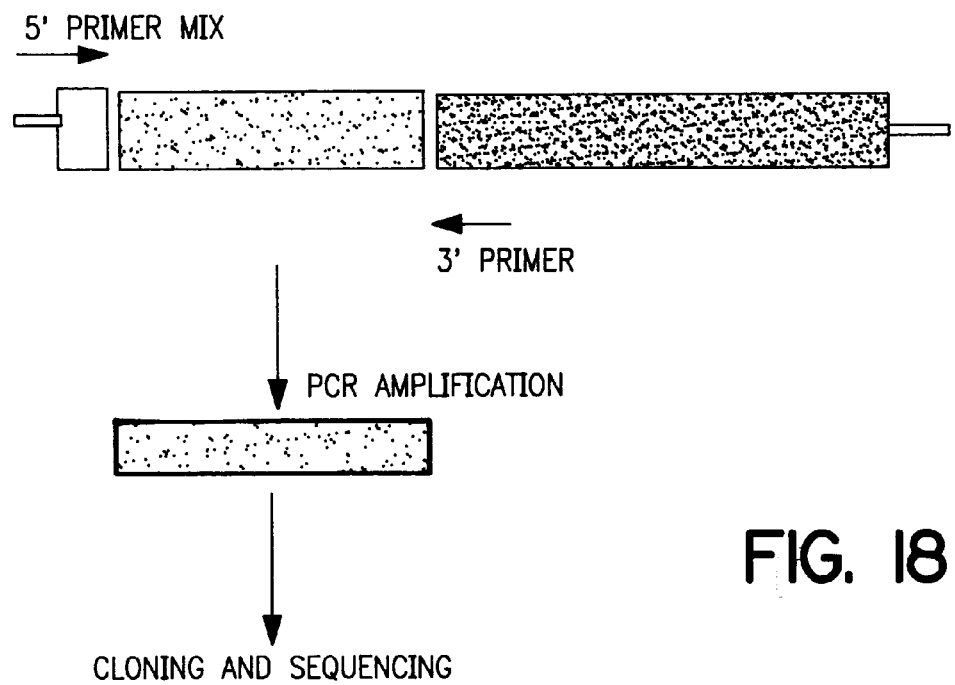
FIG. 18

ANTI-αV-INTEGRIN MONOCLONAL ANTIBODY

BACKGROUND OF THE INVENTION

Integrins are a super-family of cell surface adhesion receptors which control the attachment of cells with the solid extracellular environment—both to the extracellular matrix (ECM), and to other cells. Adhesions is of fundamental importance to a cell; it provides anchorage, cues for migration, and signals for growth and differentiation. Integrins are directly involved in numerous normal and pathological conditions, and as such are primary targets for therapeutic intervention. Integrins are integral transmembrane proteins, heterodimers, whose binding specificity depends on which of some 14 α-chains is combined with which of some 8 β-chains. The integrins are classified in four overlapping subfamilies, containing the β1, β2, β3 or αv chains, and a particular cell may express several different integrins from each subfamily. In the last decade it has been shown that integrins are major receptors involved in cell adhesion, and so may be a suitable target for therapeutic intervention. Reports concerning integrins are given, for example, by E. Ruoslahti (J. Clin. Invest., 1991, 87) and R. O. Hynes (Cell, 1992, 69).

Except for erythrocytes, all human cells express one or more integrins. Their functions are regulated at many levels, but primarily, their ligand specificity depends on which chain associates with which β chain in the heterodimer and on the activation state of the integrins (Hynes, 1992; Diamond and Springer, 1994). The cellular background in which the integrins operate (Chan and Hemler, 1993), and the splice-variant form of the integrin which is used (Delwel et al., 1993) may also affect specificity. Given these complexities, one of the few reliable indications of integrin specificity is to directly perturb integrin function and analyze which cellular responses are affected. The history of integrin research has shown that reagents that can specifically block integrin function are decisive factors in functional analysis, from the function blocking CSAT-antibody, which first defined an integrin β1-chain (Neff et al., 1982), to the numerous vital later examples (eg. P1D6, P1B5 (Wayner and Carter, 1987), P4C10 (Carter et al., 1990), AII B2 (Hall et al., 1990), 3A3 (Turner et al., 1989), GOH3 (Sonnenberg et al., 1987), and LM609 (Cheresh and Spiro, 1987)): the field is absolutely dependent on such reagents.

The αv-series integrins are now seen to be a major subfamily, with both classical, and novel functions. As well as classically mediating cell attachment and spreading (Pytela et al., 1985; Cheresh, 1991), αv integrins have also been implicated in cell locomotion (Seftor et al., 1992), in receptor internalization (Panetti and McKeown Longo, 1993a; Panetti and McKeown Longo, 1993b), as virus co-receptors (Wickham et al., 1993), in management of the extracellular protease cascades (de Boer et al., 1993), and as regulators of tumor progression (Felding-Habermann et al., 1992). The specificities of the five known αv-series integrins, αvβ1 (Zhang et al., 1993), -β3 (Pytela et al., 1985; Cheresh et al., 1987), -β5 (Cheresh et al., 1989), -β6 (Busk et al., 1992) and -β8 (Moyle et al., 1991), have been partially defined, and they seem to exclusively recognize ligands bearing the RGD (-NH-arginine-glycine-aspartic acid-CO-) tripeptide sequences, including those in vitronectin (αvβ1, αvβ3, αvβ5), fibronectin (αvβ1, αvβ3, αvβ5, αvβ6), and von Willebrand factor, fibrinogen, and osteopontin (αvβ3) (e.g. 1991; Busk et al., 1992; Zhang et al., 1993; Denhardt and Guo, 1993; Smith and Cheresh, 1990;). Dimers with related specificities may be co-expressed on the same cell (eg. αvβ3 and αvβ5—for vitronectin on M21 cells) (Wayner et al., 1991), but may control independent functions. However, the overlapping ligand specificities within the αv-family itself and also between αv- and β1-series integrins, means that assigning a function to a defined receptor within a particular cellular environment is problematic. Function blocking antibodies have been vital in clarifying the function of αvβ3 (Cheresh and Spiro, 1987; Chuntharapai et al., 1993) and αvβ5 (Wayner et al., 1991).

However, for the other αv-integrins, no antibodies which specify the complex and perturb function are known. In particular, few reagents which specify the αv-chain of the complex, and perturb integrin function of the whole family are available. Lehmann et al. (1994) disclosed an αvβx antibody which shows no reversal of cell matrix interaction and no tumor development blocking activity.

Therefore there is intense interest in the function of αv-series integrins in tumor development. Human malignant melanoma is an increasingly prevalent aggressive skin cancer. Elevated levels of integrins α2β1 (Danen et al., 1993; Etoh et al., 1992), α3β1 (Natali et al., 1993; Yoshinaga et al., 1993), α4β1 (Hart et al., 1991), and α6β1 (Hart et al., 1991) have each been implicated in melanoma progression, but the integrins most consistently implicated are those of the αV-series. In particular, both the invasion from the primary tumor and distant metastases are characterized histologically by an increased expression of αvβ3 integrin, the "vitronectin receptor". Primary non-invasive tumors and non-malignant melanotic nevi express little detectable αvβ3, a receptor rare in healthy adult tissue (Brooks et al., 1994; Buck et al., 1990; Pignatelli et al., 1992; Lessey et al., 1992; Korhonen et al., 1991; Nesbitt et al., 1993). Immunohistochemistry of staged tumors and metastases showed a progressive increase in αVβ3 with invasive stage (Albelda et al., 1990; Si and Hersey, 1994), screening of melanoma lines uniformly reveals a high expression of αV-series integrins (Sanders et al., 1992; Gehlsen et al., 1992; Marshall et al., 1991), and in addition sprouting blood capillaries express αvβ3 during tumor angiogenesis (Brooks et al., 1994).

Studies in vivo also implicate αVβ3 in melanoma development. In the murine B16-F10 melanoma system, experimental lung metastasis could be suppressed by high levels of RGD-peptides (Hardan et al., 1993; Humphries et al., 1986), potent blockers of αv-integrin function. More recently, Felding-Habermann and colleagues have shown that αV-series integrins promote subcutaneous tumor growth of M21 human melanoma in immune-deficient mice. The M21 system is elegant, and consists of a suite of cells expressing different αV-series integrins (Kieffer et al., 1991; Felding-Habermann et al., 1992; Cheresh and Spiro, 1987). The parent, M21, expresses αVβ3 and αVβ5 (Wayner et al., 1991): it attaches to vitronectin and grows as a subcutaneous tumor. M21-L, a somatic variant of M21, has no detectable αV (Cheresh and Spiro, 1987): it cannot bind vitronectin and develops slow-growing tumors. M21-L4 is a transfectant of M21-L, stably re-expressing a full length αV-chain: it binds vitronectin and grows rapidly as a subcutaneous tumor (Felding-Habermann et al., 1992). Thus the presence of cell surface αV-integrins is directly correlated with M21 subcutaneous growth.

However, M21 was subjected to extreme selection pressures during the establishment of the variant lines M21-L and M21-L4. In this invention, it was found that αv-integrin function on the native M21 population can be blocked and that a surprising effect on cell behavior and tumor development can be found. Peptidic antagonists can be synthesized easily, however, their use is restricted because of their poor bio-availability, short half life in vivo, and rapid clearance from the animals (Humphries et al., 1988). Syngeneic antibodies offer an interesting alternative to peptides. They have a long half life in-vivo (Tao and Morrison, 1989; Haba et al., 1985) and their binding specificities can be well demonstrated by standard techniques. Unfortunately, although there are excellent αV-specific antibodies such as LM142 (Cheresh and Spiro, 1987), there are few that effectively block αV-integrin functions.

The specificity and biological function of the αv-family members is much debated, primarily because no reagent yet exists that will knock out the function of the whole class—there exists no potent αv blocking antibody. The revelation that the classical adhesion receptors of the integrin family support other less conventional biological functions has intensified the search for their molecular mechanisms of action. The search has revealed several unpredicted regions on the integrins that allosterically report their activation state, or, when ligated, can themselves activate integrin function. Inhibitors of integrin function, by contrast, generally occlude the active site, the classic example being RGD-peptides that replicate the integrin recognition site of many ligands of integrins of the αv-series and of 5β1. Such a reagent would be very useful, not only to help elucidate these specificities and functions, but would also have potential therapeutic and diagnostic utility.

SUMMARY OF THE INVENTION

The invention relates to a novel monoclonal antibody and a hybridoma cell line producing said antibody. The monoclonal antibody, a preferred embodiment of which is named 17E6, has the following properties:

reacting only with the αV-chain of human αV-integrins, blocking the attachment to the integrin substrate of the αV-integrin bearing cell, triggering reversal of established cell matrix interaction caused by αV-integrins, blocking tumor development, and showing no cytotoxic activity.

The object of the invention is, therefore, a monoclonal antibody having said properties.

In addition, object of the invention is a monoclonal antibody producing hybridoma cell line having the designation 272-17E6 and deposited under accession number DSM ACC2160, as well as a monoclonal antibody having the properties given above and which is obtainable by said hybridoma cell line.

Furthermore, the invention relates to DNA sequences and amino acid sequences. The DNA sequences are coding for the antibody or parts of it. The sequences are given in FIG. 17a and 17b and in the attached Sequence Protocol.

The object of the invention is, finally, a pharmaceutical composition comprising an antibody as defined above. Upon further study of the specification and appended claims, further objects and advantages of this invention will become apparent to those skilled in the art.

This invention describes such a novel function-blocking antibody directed against the human αv-integrin chain, which is designated 17E6. Many reports have discussed the irreversible nature of the interaction between αvβ3 and its ligand, for example, vitronectin. Here it is revealed that 17E6 will rapidly trigger the reversal of this so-called irreversible interaction between αv-series integrins and their substrates, suggesting therapeutic applications. This invention analyzes the mechanism of action of 17E6 and found it an extremely poor competitor for ligand binding to αvβ3, while vitronectin and RGD-based active site probes compete strongly for one another at the receptor. And other antibodies compete strongly for 17E6. Thus, 17E6 acts as an allosteric inhibitor. Cross-linking experiment reveal that αvβ3, but not αvβ1 or αvβ5, needs to be dimerized before 17E6 can block. This discovery reveals that 17E6 functions by a novel mechanism involving a manipulation of integrin-induced signal transduction pathways. The antibody according to the invention blocks tumor development, and has, moreover, no cytotoxic activity.

BRIEF DESCRIPTION OF THE DRAWINGS

Various other objects, features and attendant advantages of the present invention will be more fully appreciated as the same becomes better understood when considered in conjunction with the accompanying drawings, wherein the figures show the following.

Viable M21 melanoma (A) were cell-surface labelled with biotin, extracted with detergent, and immunoprecipitated and resolved on non-reducing 7.5% SDS-PAGE. Standards were run in lane a and weights in KDa shown to the left. Precipitation was with the control antibodies LM142 (anti-αv: lane b) and LM609 (anti-αvβ3: lane c), and 21H6 (lane d), 10G2 (lane e), 20A9 (lane f), 23G5 (lane g), 17E6 (lane h), 14D9 (lane i), and 14E2 (lane j). LM142 and LM609 precipitate a similar pattern of proteins to 10G2, 20A9, 23G5, and 17E6, while 21H6 and 14E2 precipitate a band at ~200 KDa. 14D9 precipitates both patterns. M21 melanoma (B), M21-L αv-deficient melanoma (C), and UCLAP-3 cells (D) were cell-surface labelled with biotin, and immunoprecipitated as in (A). Precipitation was with antibodies LM142 (anti-αv: lane b), LM609 (anti-αvβ3: lane c), 17E6 (lane d), AP3 (anti-β3: lane e), and 20A9 (lane f). Molecular weight markers are run in lane a, and weights in KDa shown to the left. The position of αv, β1, β3, β5 bands is indicated.

Figure 3:
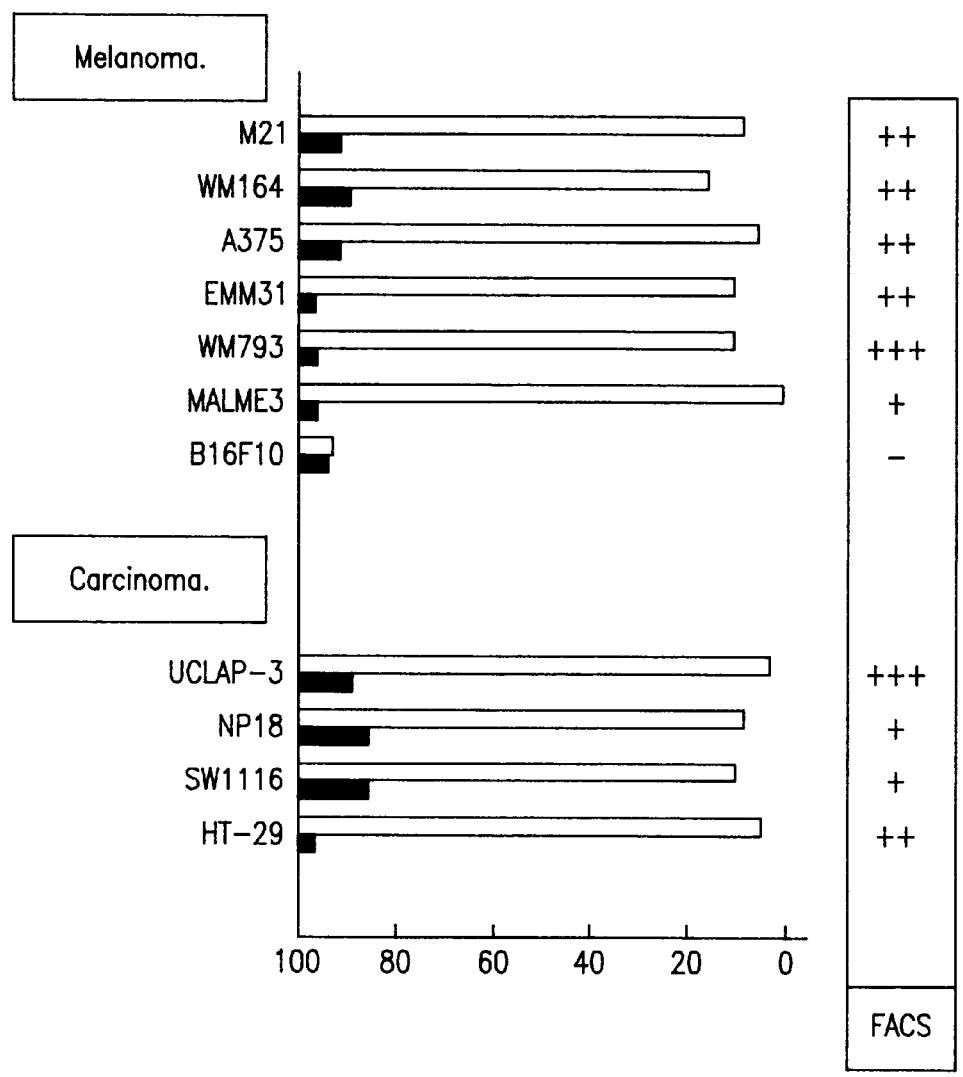

FIG. 3: 17E6 Interferes with Initial Cell Attachment to Vitronectin.

A series of melanoma lines (Mels.), and carcinoma cell lines (Cars.) were screened by FACS for reactivity with 17E6 Mab. FACS intensities were as described in Table 2. The cells were then allowed to attach to vitronectin-coated substrates (0.5 g ml$^{-1}$ coating) in the presence of hybridoma supernatants from 17E6 (open) or 14E2 (solid). After washing, attached cells were counted as described in Materials and Methods, and the data normalized to attachment in the absence of antibodies. Note that excepting B16F10 (murine melanoma), all cells were of human origin. Malme 3 is a fibroblast line. Absolute percentage of cells attached in the absence of antibodies was for M21 (70%), WM164 (68%), A375 (75%), EMM31 (67%), WM793 (65%), MalMe3 (67%), B16F10 (70%), UCLA-P3 (76%), NP-18 (65%), SW1116 (68%), HT29 (65%). Horizontal axis: cell attachment in % of control.

FIG. 4: 17E6 Perturbs Adhesion Mediated by both $\alpha v\beta 3$ and $\alpha v\beta 5$ Integrins.

Purified monoclonal antibodies (Mab) or mouse ascites were co-incubated during cell attachment to vitronectin-coated substrates (5 mg ml$^{-1}$). Cell lines (A,B) M21; (C, D) UCLAP-3; (E,F) WM-793. Symbols represent the following antibodies (specificities): (●)=17E6 ($\alpha v$); (▲)=LM609 ($\alpha v\beta 3$); (◆)=14D9.F8 ($\alpha v$); (○)=P4C10 ($\beta 1$); (□)=P5H9 ($\alpha v\beta 5$); (▽)=P5H9+LM609 [dilution starting at 10 g ml$^{-1}$] ($\alpha v\beta 3$+$\alpha v\beta 5$). Vertical axis: cells attached (%). Horizontal axis: left side: Mab (g/ml), right side: ascites dilution (1/×).

Figure 5A:
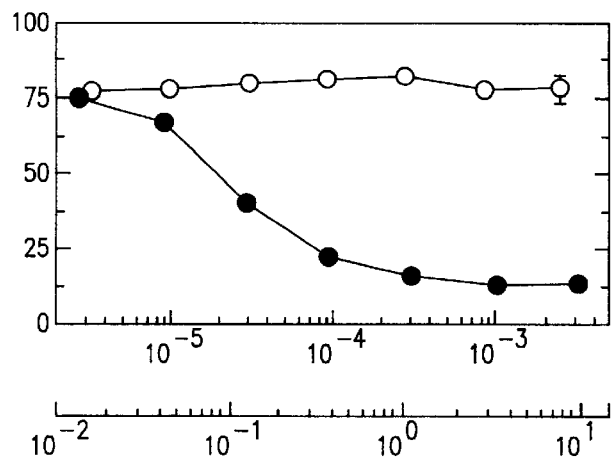
Figure 5C:
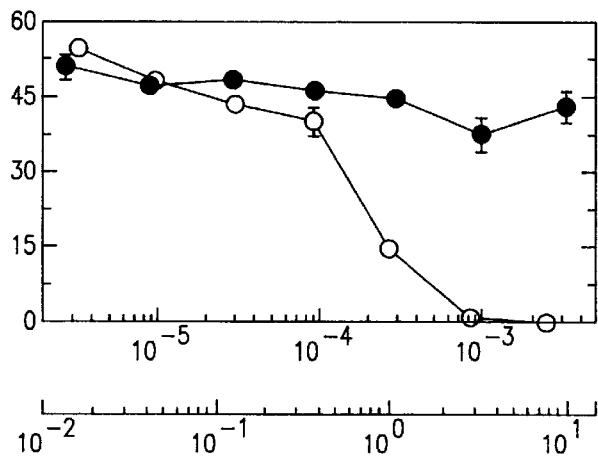
Figure 5C:
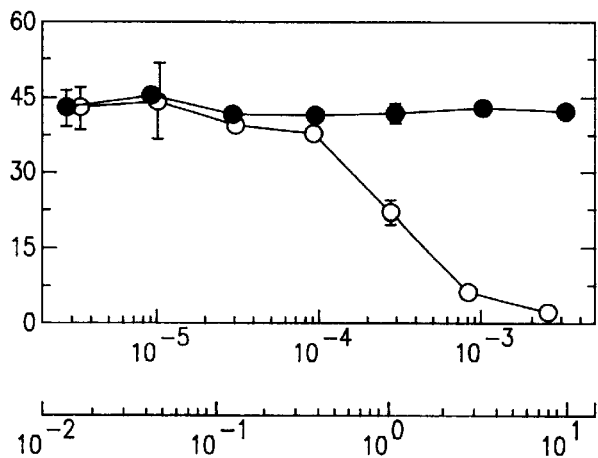

FIG. 5: 17E6 Perturbs Adhesion to Vitronectin but not to Other Matrix Components.

The effect of 17E6 ($\alpha v$,●) and P4C10 ($\beta 1$, ○) on cell attachment to vitronectin (A), laminin (B) or collagen type I (C) was studied. Only on VN coated surfaces did 17E6 block cell attachment. Only on collagen type I and laminin did P4C10 block cell attachment. Horizontal axis: P4C10 dilution(1/×) (upper axis) and Mab (g/ml) (lower axis); vertical axis: % cells bound.

Figures 6A, 6B, 6C, 6D, 6E, 6F, 6G, 6H:
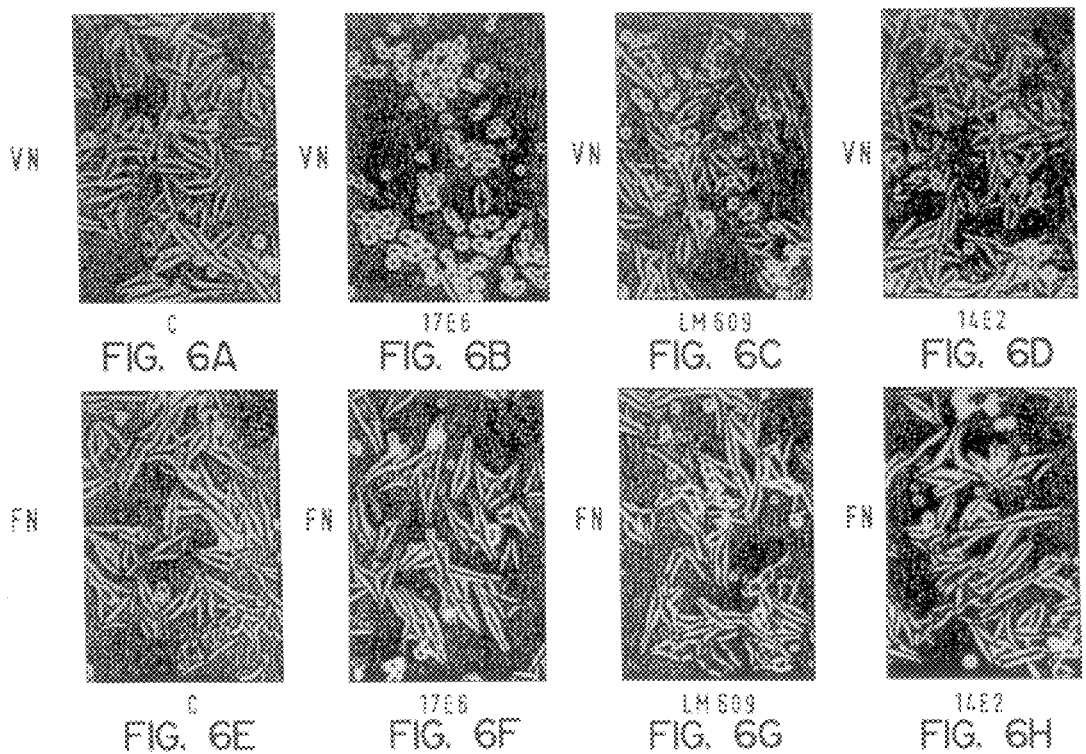

FIG. 6: 17E6 Reverses Established Cell-Vitronectin Contacts.

M21 melanoma were allowed to attach for 24 h to surfaces coated with vitronectin (VN—upper row) or fibronectin (FN—lower row). The cells attached within 30 min and were well spread, and proliferating by 24 h (a,e) when 17E6 was added to the culture medium (b,f). After 30 mins on vitronectin (b) cells rounded, while on fibronectin (f) they remained spread. LM609 (c, g) and 14E2 (d,h) had little effect on either substrate. Antibody concentrations: (b): 0.1 g ml$^{-1}$. (c,d,f–h): 100 g ml$^{-1}$.

FIG. 7: M21 human melanoma development in BALB/c nude mice is modulated by $\alpha v$-integrins.

A.B. Effect of 17E6 on Subcutaneous M21 Development.

0.5×10$^6$ M21 (A.) or M21-L (B.) were incubated with buffer (○), 17E6 (●) or 14E2 (△) antibodies and injected subcutaneously into nude mice. With time, the tumor dimensions were measured and the volume plotted. A typical experiment is shown. Error bars show the s.e.m. from 8 animals per group. Vertical axis: tumor volume (mm$^3$), horizontal axis: days post injection.

C. Effect of $\alpha v$ on M21 Experimental Metastasis.

0.32×10$^6$ (◆,■) or 1×10$^6$ (◇,□) of M21 (◆,◇) or M21L (■,□) cells were injected into the tail vein of nude mice. At the time shown, groups of animals were killed and the lungs examined for tumor nodules. All the M21 mice were killed at 42 days. For the M21-L mice, 3–6 mice were sacrificed at each point. The tumor burden after 6 weeks in the M21 mice was too high to count (>>250 per lung), so T-statistics are shown for the hypothesis that an M21-L group is from the same population as the control M21 group at 42 days at the <0.001 level (**) or <0.02 (*). Where both hi and lo injected groups have the same significance only one is shown. The bars show the mean tumor number for the groups. Vertical axis: metastases/lung; horizontal axis: days post injection.

FIG. 8: 17E6 is not cytotoxic.

A. Effect of 17E6 on M21 Cell Proliferation.

5×10$^4$ M21 were seeded in DMEM/FCS with carrier, (○), or in the presence of 50 g ml$^{-1}$, 17E6 (●) or 14 E2 (△) antibodies and the cell numbers were counted daily. Kinetics and saturation density of proliferation are unaffected by the antibodies. Vertical axis: cell number; horizontal axis: days.

B. 17E6-dependent Lysis of M21 Cells by Microglial Cells.

Thymidine labelled M21 cells were mixed with BALB/c-derived microglial brain macrophages, serially diluted antibodies were added, and following incubation, thymidine release was measured. Controls: (△) M21 cells alone; (◆) M21+17E6 (100 nM); (◇) M21+14.18 G2a; (▲) M21+microglia. Mean±s.d. (n=6). Experimentals: (●) M21+microglia+17E6; (□) M21+microglia+14.18 G2a. 17E6 did not induce antibody-dependent cell lysis. Mean±s.d (n=3). Vertical axis: cytotoxicity (%); horizontal axis: antibody concentration (M).

C. 17E6-dependent Cytostasis of M21 Cells by Microglial Cells.

M21 cells were incubated with microglial cells and serially diluted antibody, and then pulsed with [H$^3$]-thymidine to measure DNA synthesis. Thymidine incorporation ([H$^3$]-thy) was measured. Symbols as in B. Note the cytostatic activity of the effector cells alone (▲). Microscopic observation of the assay showed that in regions of homogeneous microglial cells at 14.18 G2a$\geq 10^{-10}$ M, no M21 cells survived. Vertical axis: [H$^3$]-thymidine incorporation (cpm× 10$^{-3}$); horizontal axis: antibody concentration (M).

FIG. 9: 17E6 does not affect DNA synthesis by M21 cells.

Cell lines (A) M21; (B) M21-L; (C) M21-L4; (D) M21-LGpIIb were cultured, and buffer (○), or the antibodies 17E6 (●), LM609 (▲) or 14E2 (△) at the concentrations shown were added. In (B) and (D), the routine positive control, taxol (◇) is shown. After 48 h, the cells were pulsed with [H$^3$]-thymidine and the incorporated radioactivity was measured.

The antibodies had no effect on DNA synthesis. Taxol completely suppresses it. cf. FIG. 8: 90, μg ml$^{-1}$ Mab=600 nM. Vertical axis: [H$^3$]-thymidine incorporation (cpm×10$^{-3}$); horizontal axis: Mab concentration (μg/ml).

Figure 10:
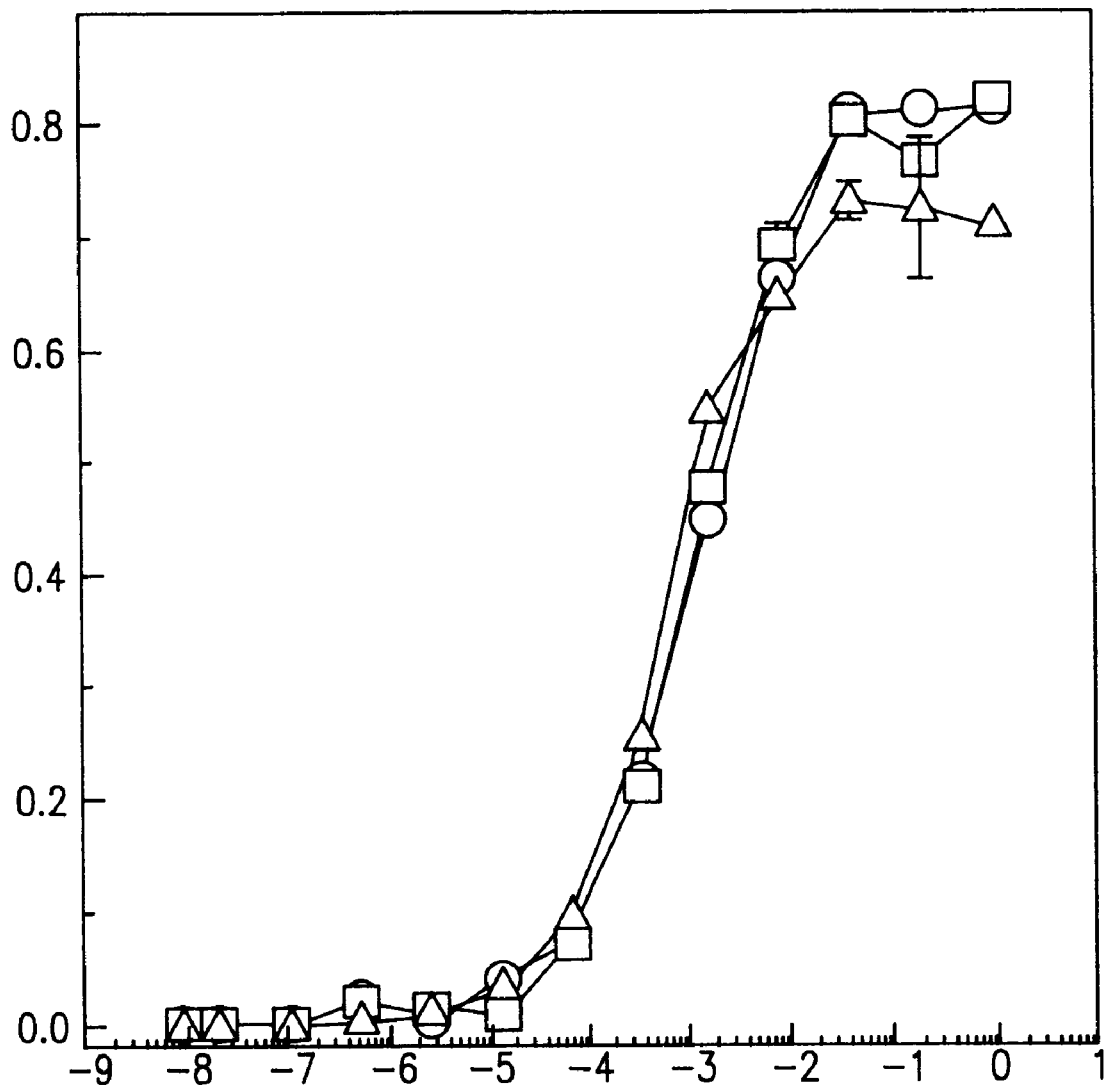

FIG. 10: ELISA of 17E6 and fragments on purified $\alpha v\beta 3$.

Intact 17E6 (△), its F(ab')$_2$ (○) or F(ab') (□) fragments at the indicated concentrations were allowed to bind plates coated at 1 mg ml$^{-1}$ with $\alpha v\beta 3$ and bound antibody was detected. Vertical axis: optical density (OD) at 450 nm; horizontal axis: antibody (log$_{10}$ μg/ml).

FIG. 11: Cell attachment mediated by $\alpha v\beta 1$ and $\alpha v\beta 5$ but not by $\alpha v\beta 3$ is blocked by 17E6 F(ab').

Cells as indicated were allowed to attach to 5 mg ml$^{-1}$ coating of vitronectin in the presence of the indicated concentrations of 17E6, its F(ab')$_2$ or F(ab') fragments. 100% attachment varied from ~85% (WM164) to ~50% (V+B2) of total cells added. Vertical axis: % maximum cell attachment; horizontal axis: antibody concentration (μg/ml).

FIG. 12: M21 attachment to vitronectin is blocked by cross-linking 17E6 F(ab').

During M21 cell attachment to vitronectin (as FIGS. 4, 11), 17E6 F(ab') fragments or intact AP3 antibody at 0 (○), 0.1 (▽), 1.0 (□), or 10 μg μl$^{-1}$ (△) were coincubated with the indicated concentrations of cross-linking anti-mouse second layer antibody. The cross linker showed identical ELISA affinities for 17E6 F(ab') and AP3, (not shown). Vertical axis: optical density (OD) at 405 nm; horizontal axis: Goat anti mouse antibody concentration (μg/ml).

Figure 13:
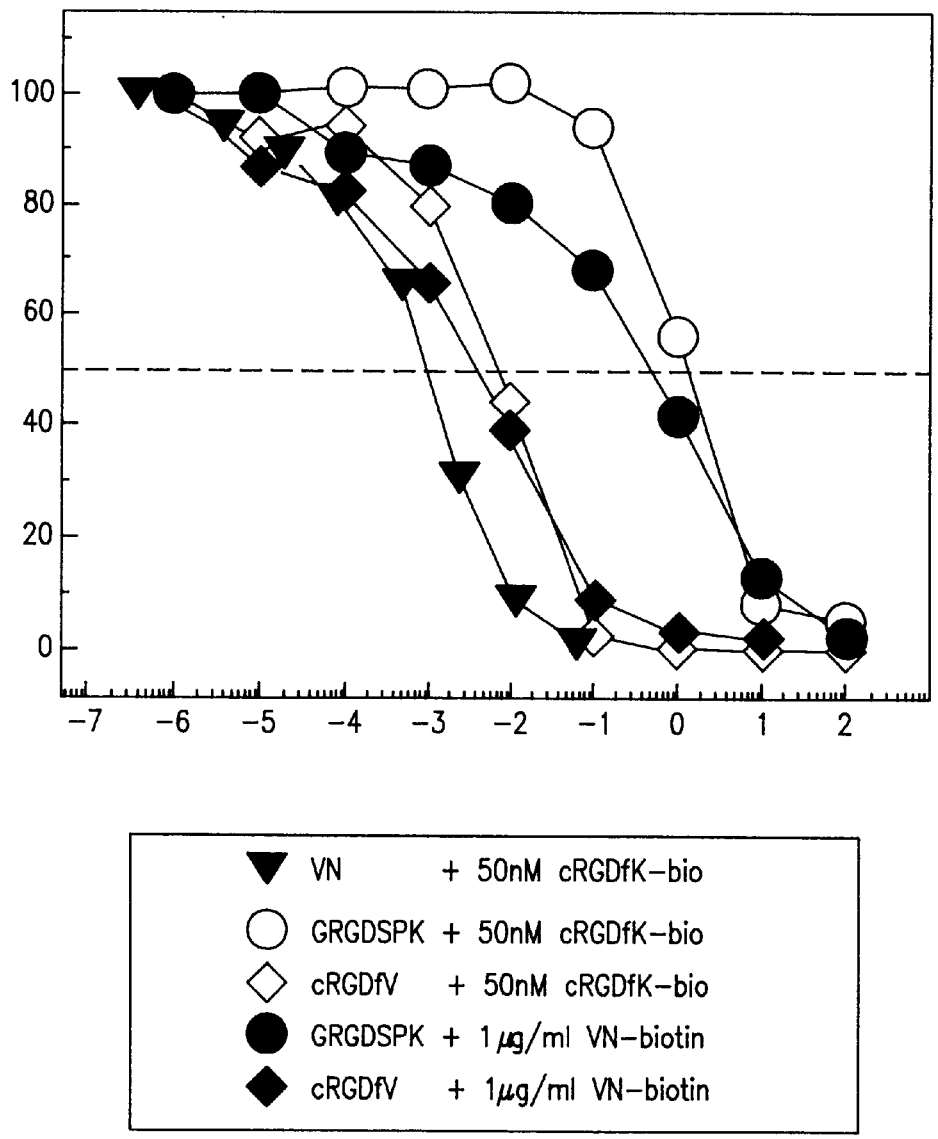

FIG. 13: Ligand active site mimetics and vitronectin compete with one another for binding to αvβ3 in direct competition assays.

Increasing concentrations of vitronectin (▽), or peptides GRGDSPK (SEQ ID NO:5) (○,●) or cRGDfV (◆,◇) were coincubated with biotinylated vitronectin (1 μg ml$^{-1}$≡1.5 nM) or a biotinylated cRGDfV derivative (cRGDfK-bio: 50 nM) on αvβ3 coated plates. Bound biotin was detected with an anti-biotin antibody. Figure assumes a mean $M_r$ for univalent multimeric vitronectin of 0.65 MDa. Vertical axis: % ligand bound; horizontal axis: peptide/VN (log [(μM)]).

Figure 14:
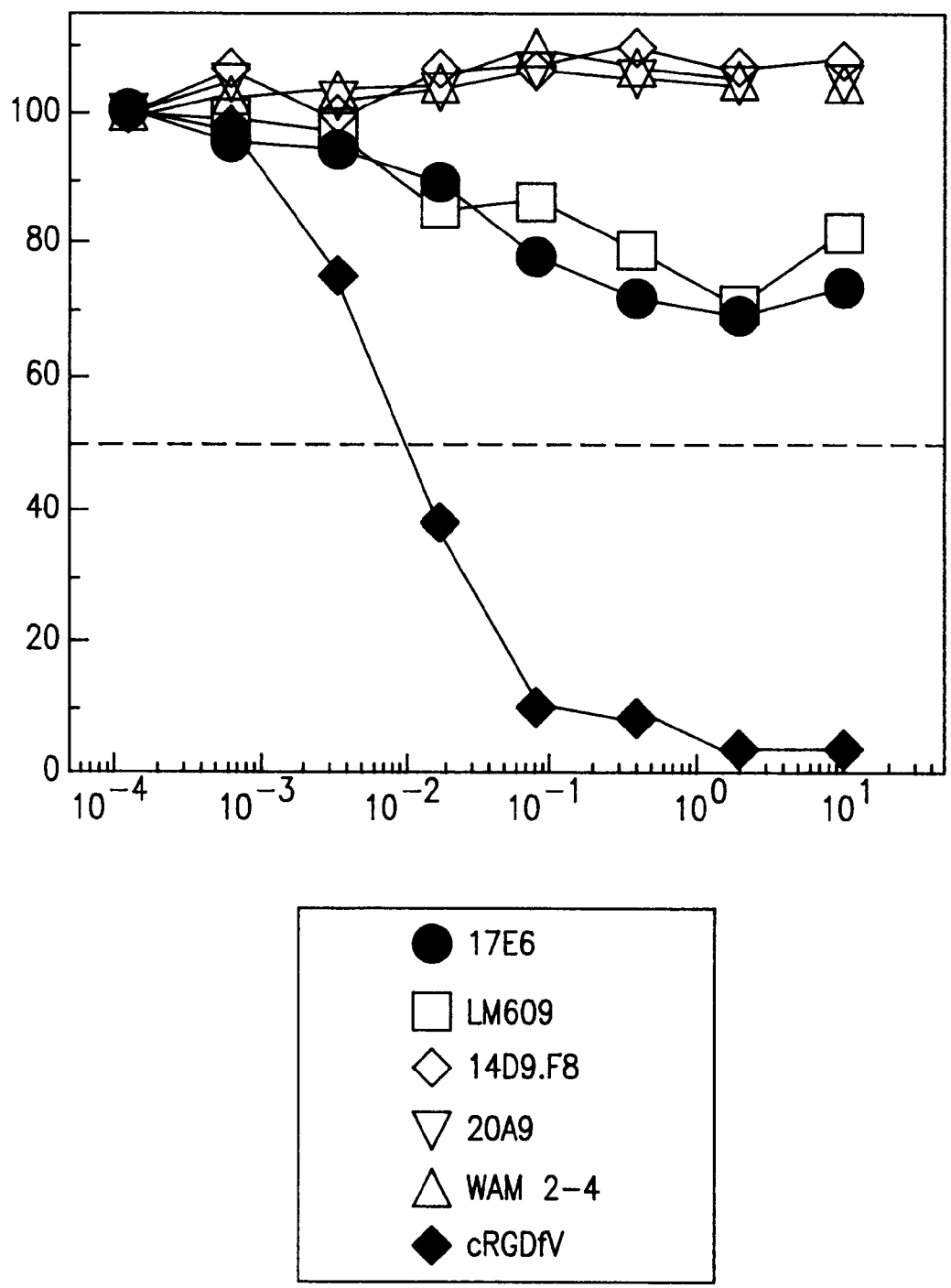

FIG. 14: 17E6 does not compete with vitronectin for binding to αvβ3 in direct competition assays.

Increasing concentrations of 17E6 (●), other anti-αvβ3 antibodies (□,◇,▽,△), or ligand mimetic cRGDfV (◆) were coincubated with biotinylated vitronectin (1 μg ml$^{-1}$) on αvβ3 coated plates. Bound biotin was detected with an anti-biotin antibody (cf. saturation profile under the same αvβ3 coating conditions for 17E6: FIG. 10.). Vertical axis: % VN bound; horizontal axis: [Mab] μg/ml-[cRGD] μM.

FIG. 15: Ligands and active site mimetics do not compete with antibodies for binding to αvβ3 in pre-block competition assays.

Increasing concentrations of vitronectin (VN,○), fibrinogen (FG,▽), fibronectin (FN,□), cRGDfV (66203,▲), or the indicated antibodies (◆) were pre-incubated for 1 h on αvβ3-coated plates and then probed by addition (no wash) with biotinylated antibody (1 μg ml$^{-1}$), as shown. Bound biotin was detected. An antibody bound value of 100% indicates that the antibody binding in the presence of the concentrations of challenger shown was as in the control without competitor. The ligands do not affect antibody binding. Vertical axis: % probe antibody bound; horizontal axis (left and right side): ligand concentration (μg/ml).

FIG. 16: Antibodies do compete with one another for binding to αvβ3 in pre-block competition assays.

Increasing concentrations of the antibodies 17E6 (●), LM609 (▽), AP3 (□) or 14D9.F8 (△), at the indicated concentrations, were pre-incubated for 1 h on αvβ3-coated plates and then probed by addition (no wash) with biotinylated antibody (1 μg ml$^{-1}$), as shown in each panel. Bound biotin was detected. An antibody bound value of 100% indicates that the antibody binding in the presence of the concentrations of challenger shown was as in the control without competitor. The antibodies compete with one another in cross-competition groups. Vertical axis: % probe antibody bound; horizontal axis (left and right side): antibody concentration (μg/ml).

FIG. 17a,b.: cDNA sequence of Mab 17E6 variable (Fv) regions: Light chain (SEQ ID NO:1): VL 17E6 light chain (a), and heavy chain: (SEQ ID NO:3) VH 17E6 (b).

The complete nucleotide (SEQ ID NO:1; SEQ ID NO:3) and the deduced amino acid sequence (SEQ ID NO:2; SEQ ID NO:4) of variable regions (including leader sequence) are shown. The leader sequences are annotated bold; the CDR sequences are in italic. The heavy chain has the characteristic structure of group II B and the light chain of kappa group V, according to Kabat classification.

FIG. 18: Schematic representation of the cloning process. mRNA encoding the Fv domains of the 17E6 antibody heavy and light chains was extracted form 17E6 hybridoma cells, transcribed into cDNA, and PCR was used to amplify out the variable regions. These were then cloned and sequenced.

DETAILED DESCRIPTION

Results

The alpha-V Group Monoclonal Antibodies React with Integrin αv-chain

Antibody screening by ELISA on purified αvβ3 and αIIbβ3 revealed five clones, 17E6, 20A9, 23G5, 14D9.F8 and 10G2 which reacted specifically with αvβ3 (Table 1). These MAbs are termed "the alpha-V group". All were IgG1 isotype. In the same ELISA assay, anti-integrin antibodies of known specificity against the αvβ3 complex (LM609), the αv chains (LM142), the αvβ5 complex (P5H9), the αIIbβ3 complex (CP8), the β3 chains (AP3) and the β1 chains (P4C10), reacted as predicted from the literature (Table 1). In ELISA on fixed cells ('CELISA'), with cells expressing αvβ3 and αvβ5 (M21), αvβ5 but no αvβ3 (UCLAP3), neither αvβ3 nor αvβ5 (M21-L), and αIIbβ3 (M21-L-IIb), the αV group showed a reaction pattern consistent with their recognition of the αv-integrin chain and clearly distinct from a reaction with β3, β5, β1, or other α-chains (Table 1).

TABLE 1

Reaction Pattern of MAbs in ELISAs and CELISAs.

| ANTIBODY | IMMUNOGEN | ISOTYPE | αVβ3 | αIIBβ3 | M21 | M21-L | M21-L-L | UCLA-P[3] | SPECIFICITY |
|---|---|---|---|---|---|---|---|---|---|
| 17E6 | αVβ3 | IgG1/k | + | − | + | − | − | + | αV |
| 20A9 | M21 | IgG1/k | + | − | + | − | − | + | αV |
| 23G5 | M21 | IgG1/k | + | − | + | − | − | + | αV |
| 14D9.F8 | M21 | IgG1/k | + | − | + | − | − | + | αV |
| 10G2 | M21 | IgG1/k | + | − | + | − | − | + | αV |
| 14E2 | M21 | IgG1/k | − | − | + | + | + | − | 200 kDa |
| 21H6 | M21 | IgG2a/k | − | − | + | + | + | − | 200 kDa |
| *LM609* | | IgG1/k | + | − | + | − | − | − | αVβ3 |
| *LM142* | | IgG1/k | + | − | + | − | − | + | αV |
| *P5H9* | | IgG1/k | − | − | + | − | − | + | αVβ5 |
| *CP8* | | IgG1/k | − | + | − | − | + | − | αIIbβ3 |

TABLE 1-continued

Reaction Pattern of MAbs in ELISAs and CELISAs.

| ANTIBODY | IMMUNOGEN | ISOTYPE | αVβ3 | αIIBβ3 | M21 | M21-L | M21-L-L | UCLA-P[3] | SPECIFICITY |
|---|---|---|---|---|---|---|---|---|---|
| *P4C10* | | IgG1/k | − | − | + | + | + | + | β1 |
| *AP3* | | IgG1/k | + | + | + | − | + | − | β3 |

Table 1
Antibodies were compared in ELISA and cell ELISA. Reagents and specificities are discussed fully in text. + = positive reaction, − = no reaction.
Key:
Antibody: Antibodies characterized in this study (bold), standard reagents (*italicized*).
Immunogen: αvβ3 = immobilized human placental integrin αvβ3. M21 = Intact M21 cells. Purified αvβ3 and αIIBβ3 were immobilized on 96-well plates for ELISA - the cell lines M21, M21-L and M21-L-IIb, and UCLAP3 were grown and fixed on the plates and tested for antibody reactivity in CELISA.
Specificity: (See text) αv = αv chain of mammalian integrins. 200 kDa = unknown 200,000 MW surface protein of melanoma cells. αvβB = integrin αvβ5. β1 = integrin β1 chain. β3 = integrin β3 chain.

The results corroborated the ELISA data with purified receptors. MAbs with specificities for β3, and GpIIb were also obtained in the screen (data not shown), and these reacted in a way clearly discrete from the alpha-v group. 17E6, 14D9.F8, 20A9 and 23G5 bound αvβ3 with similar apparent affinity. 50% binding was achieved at ~10–20 ng ml$^{-1}$ (~50–100 pM—similar to LM609). 10G2 bound similar to LM142 with about 10 times lower affinity). CP8, against αIIbβ3 and 14E2 (see below), showed minimal binding to αvβ3 at concentrations up to 100 nM.

Figure 1:
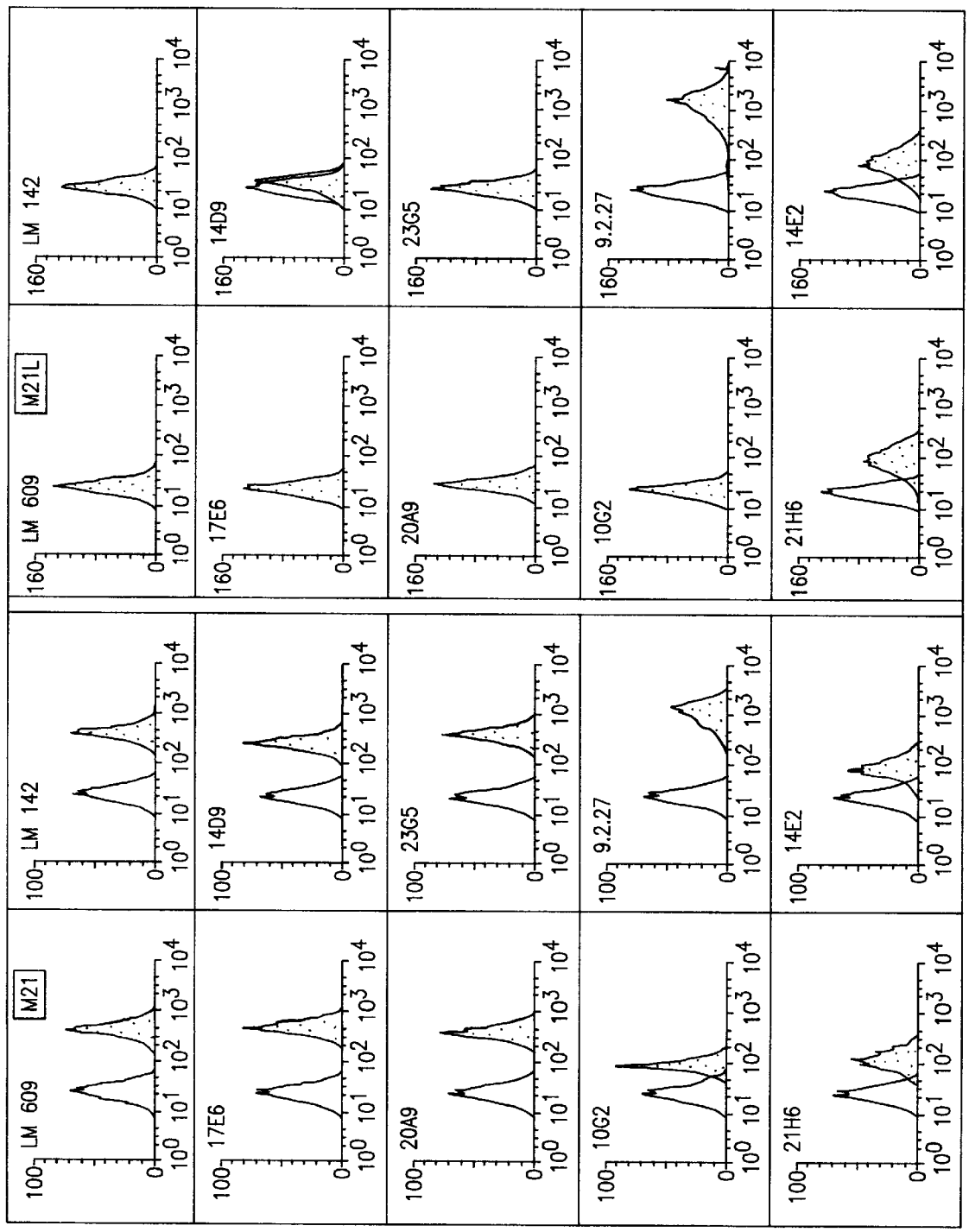
FIG. 1: Fluorescence Activated Cell Sorter (FACS) Analysis of the Alpha-V Group Antibodies and Controls to M21 and M21L Human Melanoma Cells Cells were incubated with 10 g ml$^{-1}$ primary antibodies, stained with fluorescently labelled secondary antibodies, counter stained with propidium iodide to allow gating of necrotic cells, and 10,000 cells per sample were analyzed. The open peak represents intensity of the second layer antibody alone. The closed peak, the intensity of the specifying primary and secondary together. Vertical axis shows cells per channel, horizontal axis shows log fluorescent intensity in that channel. M21 carries surface αv integrin, M21-L has none. The pattern of staining for the alpha-V group antibodies closely matches the LM142 (αv-specific) and LM609 (αvβ3-specific) stainings. Especially, they react with M21 but minimally with M21-L. Antibody 9.2.27 reacts with a surface proteoglycan. 14E2 and 21H6 recognize an otherwise undefined 200 kDa melanoma surface protein. Their staining patterns are discrete from those of the alpha-V group. Especially, they react similarly with both M21 and M21-L.

The ability of the alpha-V group to recognize native αv-integrins was tested by FACS (FIG. 1; Table 2) and by immunoprecipitation from surface labelled cells (FIG. 2). In FACS analysis (FIG. 1), the αv-expressing line (M21) reacted strongly with 17E6, 14D9.F8, 20A9, 23G5, and with the αv-defining antibodies LM142 and LM609, moderately with 10G2, and also with the control MAbs 14E2 and 21H6 and Mab 9.2.27. By contrast, αv-deficient variant (M21-L) reacted weakly with the alpha-V group and with LM142 and LM609, but showed similar reactivity as M21 with 14E2, 21H6 and 9.2.27. M21-L has an intracellular pool of β3 subunits which were detected in FACS only when the cells were permeabilized (Table 2).

Figure 2A:
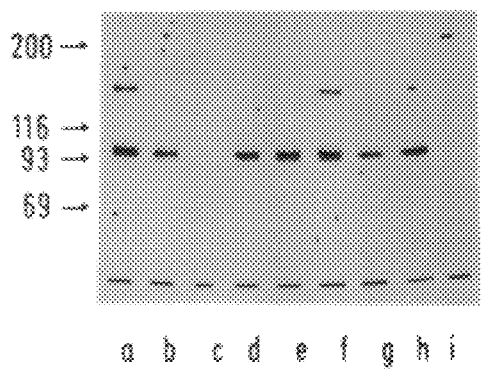
FIG. 2: The Alpha-V Group Antibodies Immunoprecipitate Similar Proteins
Figure 2B:
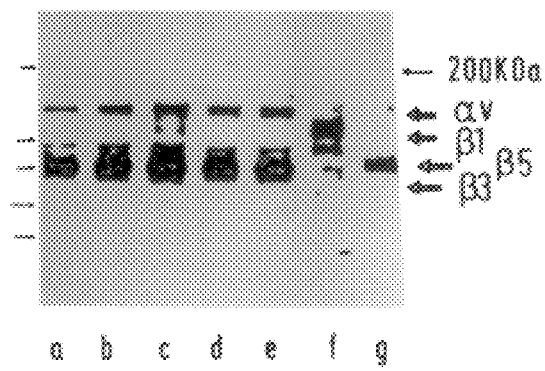
Figure 2C:
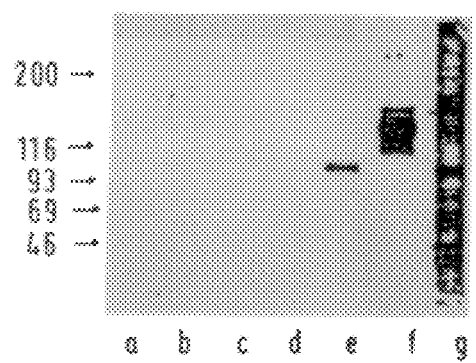
Figure 2D:
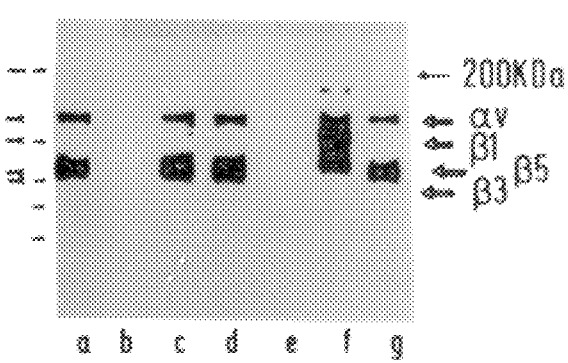

In FACS analysis of M21-L4 (αv-retransfected M21-L cells (Felding-Habermann et al., 1992)), the alpha-V group gave reaction patterns as on M21. The control vector transfectants, M21-L12 and the GpIIb transfectants, M21-L-IIb (Kieffer et al., 1991), showed no reactions with the alpha-V group (Table 1). UCLAP-3 adenocarcinoma reacted with the alpha-V group, with LM142 and P5H9, but not with LM609. UCLAP-3 does not express β3 (see Background). The melanoma WM793 had the same reaction pattern as M21. In immunoprecipitation screening of M21 cells, the alpha-V group gave the same immunoprecipitation patterns as LM142 (anti-αv), and LM609 (anti αvβ3) (FIG. 2a). A strong broad band was seen at ~92 kDa and a weaker band at ~145 kDa, with weak accompanying bands at ~100 kDa, a pattern characteristic of surface labelled αvβ3 and αvβ5 integrins (Wayner et al., 1991). When compared to the precipitation patterns on M21-L, none of the alpha-V group precipitated (data from 17E6 and 20A9 are shown), and neither did LM142 or LM609. (FIG. 2c). β1-specific antibodies gave similar precipitation patterns from both cell lines. In M21-L, precipitation with anti-β3 antibodies gave a band at ~92 kDa, due to intracellular β3-labelled in permeable (possibly necrotic) cells. UCLAP3 (FIG. 2d) gave no precipitate with LM609, but a ~95 kDa/145 kDa complex was precipitated, by the alpha-V group and by LM142 (FIG. 2d). In summary, ELISA, CELISA, FACS analyses and immunoprecipitations of gave consistent reac-

TABLE 2

Summary of Monoclonal Antibody Reactivity in Flow Cytometry

| ANTIBODY | specificity | M21 αvβ3; αvβ5 | M21-L (β3)[@] | M21-L (p) (β3)[@] | M21-L-IIb αIIbβ3 | M21-L4 αβ3; αvβ5 | M21-L12 (β3)[@] | UCLA-P3 αvβ5 | WM793 αvβ3; αvβ5 |
|---|---|---|---|---|---|---|---|---|---|
| 17E6 | αv | ++ | − | − | − | ++ | − | +++ | +++ |
| 20A9 | αv | ++ | − | − | − | ++ | − | +++ | +++ |
| 23G5 | αv | ++ | − | − | − | ++ | − | +++ | +++ |
| 14D9.F8 | αv | ++ | − | − | − | ++ | − | +++ | +++ |
| 14E2 | 200 kDa | ++ | ++ | ++ | ++ | ++ | ++ | − | +++ |
| LM609 | αvβ3 | ++ | − | − | − | + | − | − | ++ |
| LM142 | αv | +++ | − | − | − | ++ | − | ++ | +++ |
| P5H9 | αvβ5 | + | − | − | − | + | − | +++ | + |
| P4C10 | β1 | ++ | ++ | ++ | ++ | ++ | ++ | ++ | ++ |
| AP3 | β3 | ++ | − | ++ | ++ | + | + | − | + |
| CP8 | αIIbβ3 | − | − | − | ++ | − | − | − | − |

Table 2:
Levels of reactivity relative to control (secondary antibody only) were graded as follows: 1–2 (−), 2–4 (+, 4–9 (++), >9 (+++). For example, on M21, the relative fluorescent intensity of the control was typically 30–50 units, and that of LM142 binding was 300–500 units, giving mean relative reactivity around 10 (400/40).
(*) M21-L was permeabilized with 70% ethanol at −20° C.
(@)M21-L has intracellular pools of 3 chain of VNR integrin.

tion patterns and strongly suggested that MAbs of the alpha-V group react with extracellular domains on human αv-integrin chains.

Mab 17E6 is a Potent Function Blocking Antibody
17E6 can Modify Initial Cell Attachment to αv-lipands αv-integrins can function as receptors for vitronectin, so the alpha-V group was screened for their possible effects on cell attachment to vitronectin substrates. After integrin analysis by FACS, cells were tested in attachment assays (Table 2, FIG. 3). In FACS, human melanoma and carcinoma cell lines reacted similarly with the alpha-V group. The reaction with 17E6 is summarized (FIG. 3). The initial attachment to vitronectin of cells reacting in FACS with 17E6 was strongly blocked by that antibody, but only weakly affected by the control antibody 14E2 (FIG. 3). Other members of the alpha-V group were less potent (data not shown). The vigorous attachment of murine cell B16F10 on vitronectin was not affected by 17E6 and B16F10 did not react with 17E6 in FACS. As predicted (Cheresh and Harper, 1987), B16F10 attachment to vitronectin was sensitive to micromolar concentrations of RGD-peptides, suggesting the presence of functional surface αvβ3 (SLG and B. Diefenbach). Thus, 17E6 and the α-V group reacted with human but not mouse αv.

Figure 4A:
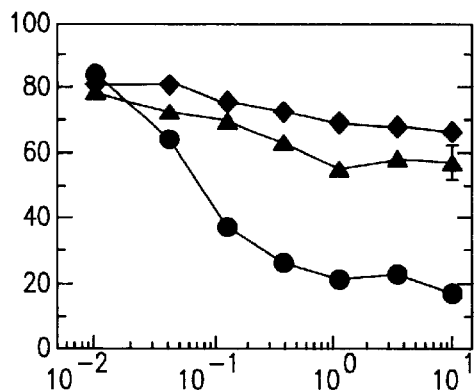
Figure 4B:
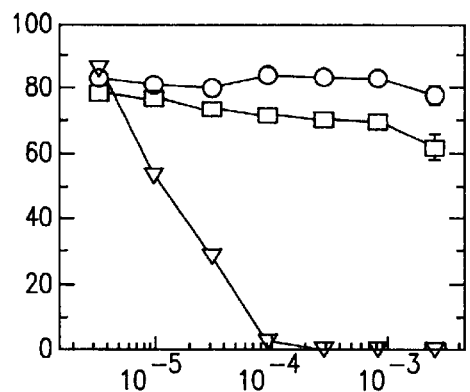
Figure 4C:
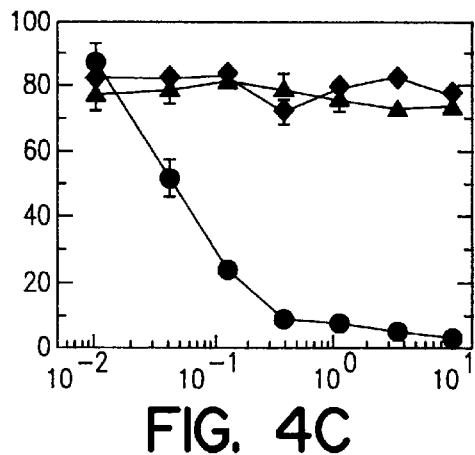
Figure 4D:
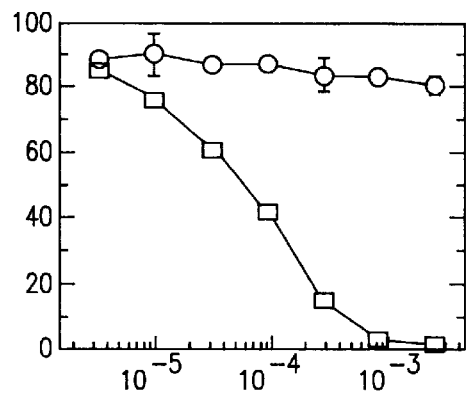
Figure 4E:
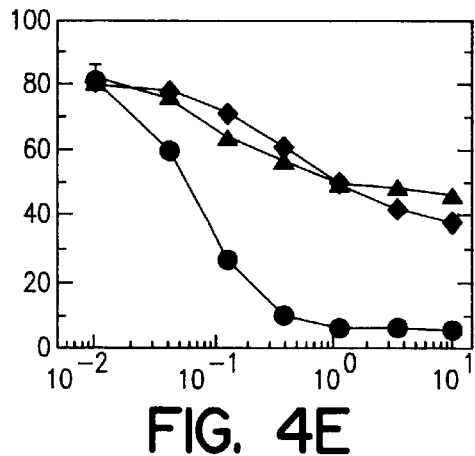
Figure 4F:
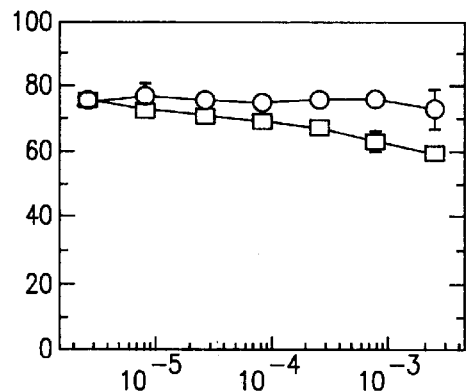

The effect of 17E6 on cell attachment was investigated. 17E6 blocked M21 attachment (~85%) to vitronectin with an $IC_{50}$ of ~0.1 g $ml^{-1}$ (FIG. 4a). This invention confirms previous studies (Wayner et al., 1991) by showing that M21 attachment was poorly blocked by antibodies to αvβ3 (LM609) or αvβ5 (P5H9) alone, but was strongly blocked when they were added together (FIG. 4a,b). Anti-β1 integrin antibodies (P4C10) had no effect on M21 attachment to vitronectin (FIG. 4b). The lines UCLAP3 and WM793 attached to vitronectin and this attachment was blocked by 17E6, and also by the complementary αvβ5-specific (P5H9/UCLAP3) or αvβ3-specific antibodies (LM609/WM793) (FIG. 4c–f). On αvβ5 (UCLAP3) 17E6 had an $IC_{50}$ of ~30 ng $ml^{-1}$. On WM793, it was ~60 ng $ml^{-1}$ and for LM609 the $IC_{50}$ was ~600 ng $ml^{-1}$. UCLAP3 expresses αvβ5 but no αvβ3 (Wayner et al., 1991), while WM793 expresses high levels of αvβ3 (Table 1). The blocking specificity of 17E6 was confirmed by its lack of effect on cell attachment to other matrix substrates (FIG. 5) P4C10 (anti-β1) abolished M21 attachment to laminin and collagen. Cell adhesion to these two substrates can be mediated by β1-series integrins (Sonnenberg et al., 1988; Takada et al., 1987).

Taken together with the biochemical data, these results are consistent with the theory that 17E6 bind the αv chain of various integrin complexes and disturbs their interaction with their ligands.

17E6 Triggers Reversal of Established Cell Matrix Interactions Mediated by αv-integrins It was next investigated whether 17E6 could affect established cell-matrix interactions. When 17E6 at low concentrations (~0.1 μg $ml^{-1}$) was added to M21 cells, it induced extensive cell rounding after 0.5–1 h at 37° C. in M21 cultures even after 24 h of attachment (FIG. 6). The effect was fully reversible and after wash out the cells returned to their spread state within 48 h. By contrast, the antibodies LM609 and 14E2 affected morphology only slightly even at high concentrations (100 μg $ml^{-1}$) . The antibodies had no morphological effects even at 100 μg $ml^{-1}$ on fibronectin coated substrates (FIG. 6 ). M21-L4 (and other cells attached via αv) were similarly affected by 17E6 on vitronectin surfaces, but not on fibronectin, collagen, or on laminin.

17E6 Blocks M21 Tumor Development in Nude Mice

Figure 7A:
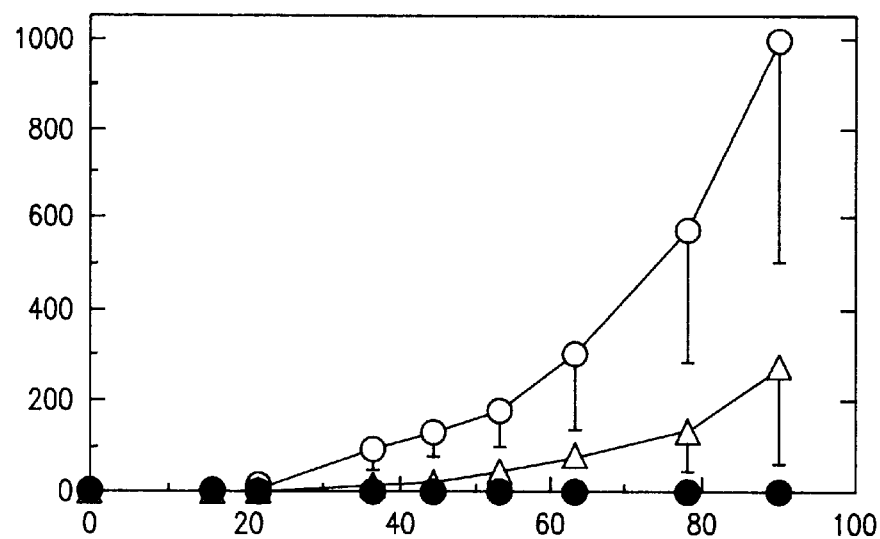
Figure 7B:
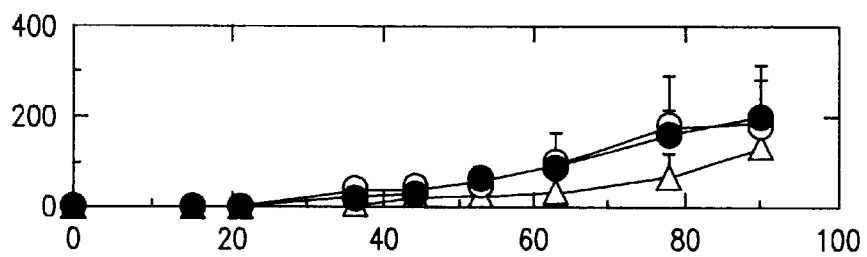

The invention investigated the effect of the αv-blocking antibody 17E6 on the subcutaneous development of M21 tumors in BALB/c nu/nu mice (FIG. 7). In animal models, the development of M21 tumors in nude mice has been correlated with the cell surface expression of αv-series integrins (see Background). M21 cells were subcutaneously co-injected and endotoxin-free antibodies. 17E6 consistently (4/4 experiments) blocked the subcutaneous development of M21 tumors (FIG. 7a). No tumors (0/32) have taken in the presence of 17E6, and the animals still remain tumor free—now in excess of 6 months. Control tumor take was 75–90%. Non-blocking antibodies against the αv-chain itself and control antibodies against the melanoma cell surface showed variable and inconsistent effects on tumor development. In 14E2 treated controls, take of tumors was reduced depending on experiment 30–60%, but remaining tumors grew as the untreated controls and, like the controls, these animals had pulmonary micro-metastases revealed when the lungs were brought into tissue culture (not shown). By contrast, 17E6 treated animals had neither subcutaneous tumors nor metastases in lungs, liver, kidney, spleen, colon, stomach, nor in thoracic or abdominal body cavities when sacrificed at 6 months. The αvβ3-deficient line M21-L grew more slowly subcutaneously than M21, and was unaffected by 17E6. M21-L controls treated with 14E2 had a take reduced in comparison to untreated animals, similar to that seen in M21 cells (FIG. 7b).

Figure 7C:
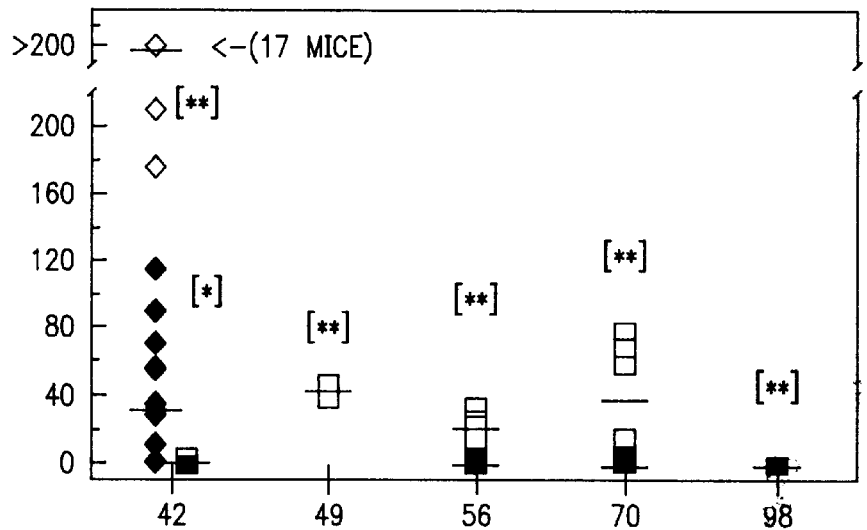

The growth of M21 and M21-L and the effect of the antibody 17E6 were compared in an "experimental metastasis" tail-vein injection model. M21 formed many colonies in a dose dependent manner, while M21-L formed significantly fewer colonies, but did form lung nodules when injected at higher dosage (FIG. 7c). In other words, tumor growth in the lungs was also enhanced by the presence of cell surface αv-integrins, and pre-incubation of M21 with 17E6 reduced (by 90%) the numbers of tumor colonies that formed. Interestingly, the level of tumor formation was similar to those achieved by M21-L cells in the same experiment. The antibody did not altering the numbers of animals in which the tumor grew (Table 3).

TABLE 3

Inhibition of development of M21 tumor foci by 17E6 Mab in BALB/C nu/nu mice lung colonization "experimental metastasis" assay.

| Cells and Treatment | Tumor Take | Number of Tumor Foci | | | % Control |
|---|---|---|---|---|---|
| | | Mean ± SEM | Median | (Range) | |
| M21 (Control) | 99 | 87 ± 110 | 30 | (3–378) | 700 |
| M21 + 17E6 | 78 | 8 ± 7.7 | 5 | (0.21) | 9 |
| M21-L | 56 | 19 ± 22 | 8.5 | (0–60) | 22* |

Table 3:
M21 and M21-L cells were harvested with trypsin/EDTA, incubated with 17E6 antibody or control antibody, washed and injected into the tail vein of nude mice. 7 weeks later the animals were sacrificed and the lungs examined for surface tumor foci. Pretreatment with 17E6 lowered the numbers of foci that developed. Similar numbers of foci developed when M21-L cells (which lack αv on the cell surface) were injected.
* = Compared to control: not antibody-dependent.

In summary, the presence of αv at the cell surface promoted M21 tumor formation in both subcutaneous and experimental metastatic models, and the αv-blocking and reversing antibody 17E6 vigorously suppressed the growth of M21. In an experimental metastasis model with M21 cells, the vigorous growth of M21 and the poor growth of M21-L closely follows the subcutaneous pattern of tumor growth and M21 growth was also suppressed by pretreatment with 17E6. This data strengthens the link between αv-integrins and the development of human melanoma.

Effects of 17E6 not Due to Cytotoxicity

Figure 8A:
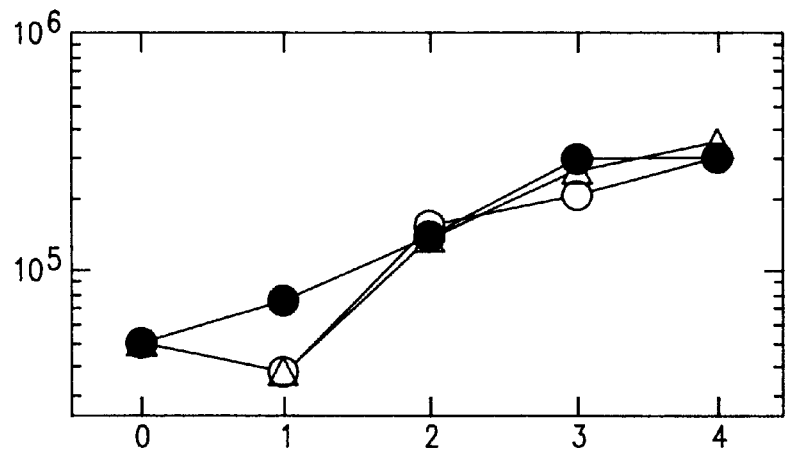

After observing its potent effects on attachment, morphology, and tumor development, it was attempted to find out the mechanism of 17E6 action. 17E6 was tested for cytotoxicity (FIG. 8). The kinetic of cell growth and the final saturation densities achieved were not greatly influenced by the presence of 17E6 or control antibody (FIG. 8a).

Figure 8B:
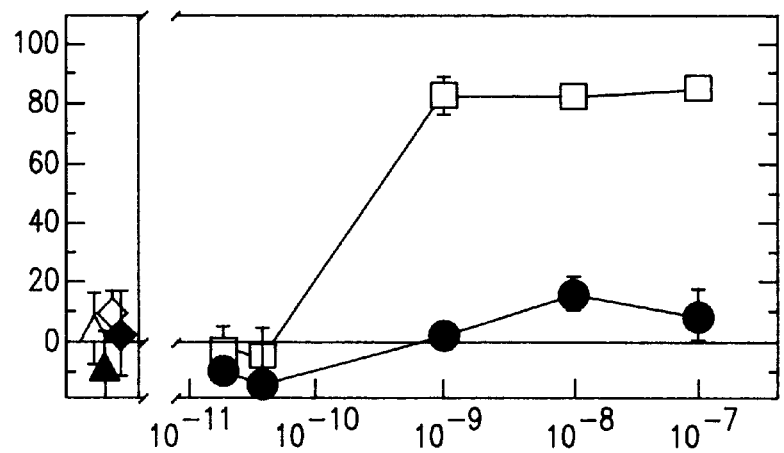

Nude mice are immune deficient. Of the few cells immune competent cells which remain, macrophages are the most likely to direct a cytotoxic, antibody mediated response. To test the possibility that the antibodies were directing cellular cytotoxicity (ADCC), murine macrophages syngeneic to the antibodies were tested in ADCC against M21 cells. As effector cells murine brain macrophages (microglia) are especially potent mediators of ADCC (Sutter et al., 1991). The positive control, Mab 14.18 G2a caused nearly complete lysis of M21 at $10^{-9}$ M, while 17E6 at up to $10^{-7}$ M did not mediate ADCC (FIG. 8b).

Figure 8C:
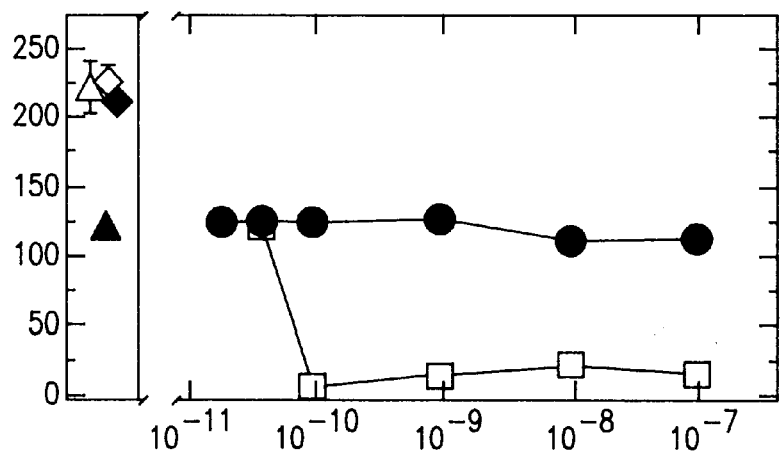
Figure 9A:
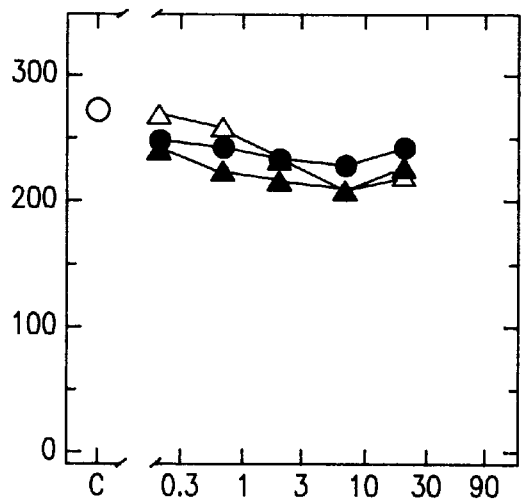
Figure 9B:
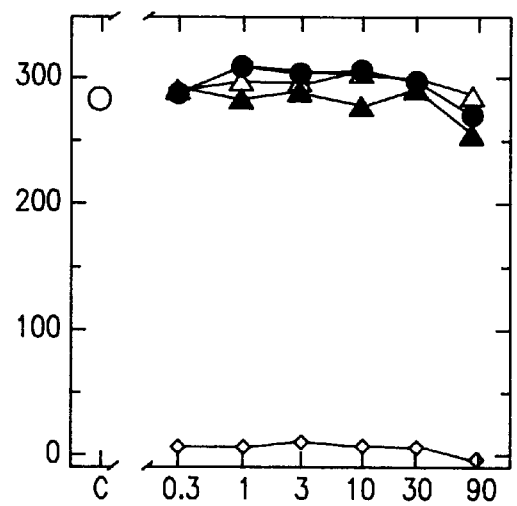
Figure 9C:
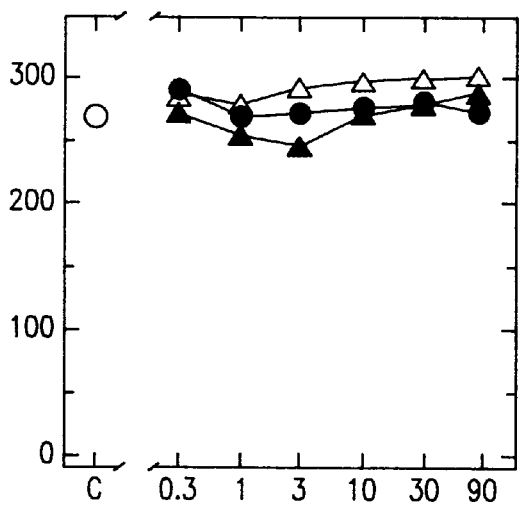
Figure 9D:
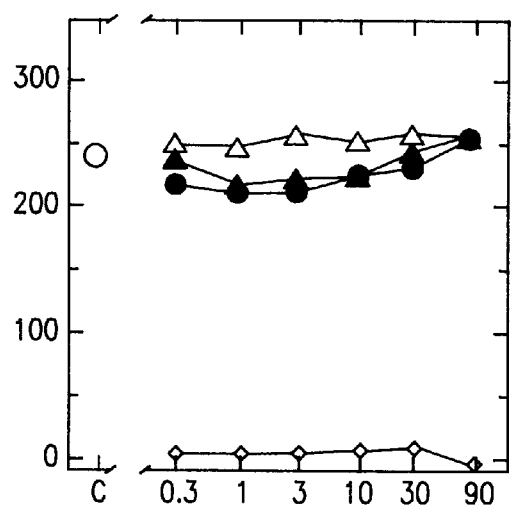

In order to evaluate if 17E6 might exert a cytostatic activity in the presence of effector cells, DNA synthesis of M21 microglial cocultures was measured in the presence of the antibodies (FIG. 8c). At $10^{-10}$ M, 14.18 G2a caused a $\geq 90\%$ inhibition in [$^3$H]-thymidine incorporation.

Having tested the effects on cell proliferation, ADCC and AECM, it was examined whether the levels of DNA synthesis in M21 cells were affected by the MAbs. 17E6, 14E2, and LM609 at 0.5 M had no effect on thymidine incorporation (FIG. 9). DNA-synthesis in M21-L, M21-L4 and M21-L-IIb cells were also unaffected by the antibodies. M21-L and M21-L-IIb react neither with 17E6 nor LM609, but do react with 14E2 (FIG. 1). Many other melanoma cell lines were also tested and their DNA synthesis was shown not to be obviously affected by the alpha-V group (not shown).

17E6 and 14E2 were IgG1 isotypes, and did not affect complement mediated lysis on M21 cells (not shown). It can be concluded that the effects of 17E6 are specific to αv-integrins, and not to drastic toxic effects on other cellular systems.

17E6 Action on Cellular αvβ3 but not αvβ1 or αvβ5 Requires Receptor Cross-linking In many biological systems transmembrane signalling is initiated by dimerization of the receptors. Indeed, multimerization of αvβ3 alters phosphotyrosinalytion patterns in HUVECs (Bhattacharya et al. 1995). It was, therefore, investigated whether receptor aggregation was involved during 17E6 action.

17E6 inhibited cellular integrins αvβ3, αvβ5 and αvβ1 (FIG. 4). Intact 17E6 and its F(ab')$_2$ and F(ab') fragments had similar binding characteristics in ELISA on isolated αvβ3 (FIG. 10), with 50% saturation being achieved at ~1 ng ml$^{-1}$ (~7 pM intact MAb). The similar ELISA titration curves suggested monovalent interaction between 17E6 and the ELISA plates. But in cell attachment assays the fragments behaved differently. The F(ab')$_2$ and intact 17E6 blocked cell attachment mediated by αvβ1 (V+B2 cells) and αvβ5 (UCLA-P3 cells) (IC$_{50}$~0.1 μg ml$^{-1}$: ~700 pM), and αvβ3 attachment (WM164 and M21 cells) (IC$_{50}$ ~0.5 μg ml$^{-1}$: ~3 nM), and the F(ab') fragment was as active as the dimeric antibodies on αvβ1 and αvβ5 (FIG. 11). However, the F(ab') fragment was at least 1×10$^4$-fold more active on both αvβ1 and αvβ5 than on αvβ3, where it only blocked 25+10% at the highest concentrations tested (50 μg ml$^{-1}$:- IC$_{50}$>>50 μg ml$^{-1}$:>>400 nM)—at these levels, irrelevant antibodies also produced similar degrees of blocking (not shown) suggesting this marginal effect to be non-specific.

A lack of biological activity of a F(ab') antibody fragment which is capable of binding (as 17E6 F(ab'): (FIG. 10)) is a classic indicator that dimerization is necessary for antibody mediated function. To confirm that cross linking was indeed necessary for 17E6 action on αvβ3, 17E6 F(ab') was cross-linked during the cell attachment assay by addition of a polyclonal anti-F(ab') antibody. A classical prozone-like effect was observed where at critical concentrations of both primary and secondary antibodies, and only then, a strong inhibition of cell attachment was observed. High quantities of second layer antibody alone or of F(ab') alone did not affect cell adhesion. Furthermore, the effect was not the non-specific result of cross-linking αvβ3 integrins: cross linking of αvβ3 by the binding but non-inhibitory antibody AP3 had no effect on cell attachment, (FIG. 12). The concentrations of F(ab') active after addition of secondary antibody in the cross-link experiments, coincide with the IC$_{50}$ of intact 17E6 on αvβ3-mediated attachment (cf. FIG. 11).

Together, these data indicate that cross linking of αvβ3 integrin is necessary to prevent WM164 and M21 attachment on the cognate ligands, while αvβ5 and αvβ1 do not require cross linking to be inactivated.

17E6 is a Poor Blocker of Receptor Function in Isolated Receptor Assay

The unusual nature of 17E6 function on αvβ3 was studied in detail in isolated receptor assays. The contrast between classical active site blockers and 17E6 are marked. Vitronectin binding to αvβ3 saturates at ~5 μg ml$^{-1}$ (~10 nM: assuming average vitronectin multimer size of 10 monomers) (FIG. 13), and this binding is specifically competed with both classical linear ligand mimetic peptides (GRGDSPK (SEQ ID NO:5): IC$_{50}$ ~2 M) and cyclized peptides (cRGDfV: IC$_{50}$ ~5 nM). By using a biotin labelled variant of cRGDfV, cRGDfK-biotin, it was possible to demonstrate directly that not only would the inhibitors compete for vitronectin binding but that vitronectin would compete for the inhibitor binding (FIG. 13), i.e., the system was symmetrical. Indeed, vitronectin, GRGDSPK (SEQ ID NO:5) and cRGDfV each competed for one another and did so both "rationally" and "symmetrically", in that the IC$_{50}$ for competition mirrored the IC$_{50}$ for inhibition of vitronectin binding to the αvβ3 complex (FIG. 13).

17E6 binding saturates αvβ3 at 0.01–0.1 μg ml$^{-1}$ (700–70 pM) (cf. FIG. 10). However, the antibody is only a weak inhibitor of ligand binding: Even at 70 nM antibody there was less than 30(+10)% inhibition of vitronectin binding. LM609 behaved in a similar way, while the αvβ3-binding non-inhibitory antibodies (14D9.F8, 20A9 and WAM2-4) were ineffective. The ligand mimetic cyclic peptide cRGDfV efficiently blocked receptor-ligand interaction (IC$_{50}$ ~10 nM) (FIG. 14) but does not affect 17E6 binding. Neither intact nor monovalent 17E6 inhibited (not shown).

17E6 Binds αvβ3 in the Presence of Saturating Amounts of Challenging Ligand

The weak competition of 17E6 for ligand in the isolated receptor assay and the availability of strong competitive inhibitors like cRGDfV raised the question of how 17E6 was affecting αv-function. The blocking activity of 17E6 and its fragments in cellular attachment assays for αvβ3 integrin requires cross linking, behavior not wholly compatible with an inhibition by competition. It was next investigated whether ligands of αvβ3 interfered directly with 17E6 binding.

Ligands were pre-bound to the receptor, and low concentrations of directly labelled 17E6 were added (FIG. 15). The binding of 17E6 was not affected (<10% block) by high concentrations of vitronectin, fibronectin or fibrinogen (all native ligands of αvβ3 {Cheresh and Spiro, 1987}) 100-fold in excess of those needed to saturate specific binding sites on αvβ3. By contrast pre-bound-17E6 competes strongly for binding of subsequently added labelled 17E6 (FIGS. 15, 16), and the native ligands of αvβ3 also compete well for one another (not shown). This falsified our assumption that 17E6 competed with vitronectin for the αvβ3 active site. Furthermore, the strong active site competitors, like the cyclic peptide cRGDfV at 200 μM also have no effect on 17E6 binding, yet block vitronectin binding to αvβ3 with an $IC_{50}$ of 2 nM (FIG. 13).

The ELISA data (FIG. 10) indicated that 17E6-αvβ3 interactions were monovalent, which reduces the possibility that a competition artefact was observed due to very high antibody affinity combined with low ligand affinity. However, other αv- and β3-specific antibodies were labelled and used these to challenge pre-bound ligand (FIG. 15), including the antibodies themselves (FIG. 16). The antibodies successfully competed for one another and clearly fell into cross competition groups (FIG. 16). The β3-specific antibody AP3 competed its own binding but did not affect the binding of and was not affected by antibodies specific either for the αvβ3 complex (LM609) or the αv-chain alone (17E6, 14D9.F8); LM609, 17E6 and 14D9.F8 all cross-competed strongly. By contrast, the pre-bound ligands did not affect 17E6 binding to αvβ3. It must be concluded that 17E6 did not function by direct competition for the ligand binding site.

Cloning and Sequencing of 17E6 Variable Regions

A primer library designed for PCR amplification of immunoglobulin variable regions was used to clone immunoglobulin enriched cDNA libraries for the heavy and light chain regions of the hybridoma 17E6. The redundant variable region primers terminated at the start of the leader. The constant region reverse primers terminated 30 bp into the constant region. The primers were designed with terminal SalI or XmaI restriction sites for cloning. PCR products of the expected size (420–450 bp (Jones and Bendig, 1991)) were obtained, cloned and sequenced (FIG. 17). The 17E6 immunoglobulin light chain variable region, VL17E6, was 381 bp in length. The heavy chain variable region, VH17E6, was 411 bp in length. The heavy chain variable sequences were characteristic of Kabat group IIb immunoglobulins and the light chain sequences characteristic of Kabat group V (Kabat et al., 1987). The cloning strategy is shown schematically (FIG. 18).

Tumor progression and metastasis is classically a disease where cells escape normal growth and adhesion controls and invade, migrate, attach and grow at an inappropriate site. Integrins are now known to control many cell adhesion events, and adhesion can in turn regulate mechanistically interwoven events including growth, differentiation, cell movement and the activity of protease networks, developmental events which are reiterated in the metastatic cascade (Liotta et al., 1991; Stetler Stevenson et al., 1993; Fidler, 1988). In this study antibodies are described directed against human αV-series integrins one of which, 17E6, perturbs initial cell attachment, disrupts stable αv-ligand interactions and interferes with human melanoma development in an in vivo animal model (Fidler, 1986). In biochemical analyses the alpha-V group antibodies showed reaction patterns closely related to LM142—a well defined antibody body to human αv—but distinct from the reaction patterns of αVβ3-specific (LM609), αVβ5-specific (P5H9) and from other defined anti-integrin antibodies. Thus, the alpha-V group antibodies are likely to recognize the human αV-integrin chain. cDNA cloning of the 17E6 immunoglobulin transcripts revealed unique, unambiguous sequences. The heavy chain variable sequences were characteristic of Kabat group IIb immunoglobulins and the light chain sequences characteristic of Kabat group V (Kabat et al., 1987). Thus, the antibody is uniquely defined.

Discussion

17E6 strongly perturbed cell interactions mediated by αV. Antibodies that perturb function have been vital to our understanding of integrin function, but the αV-field has lacked a potent class-specific blocking antibody. 17E6 blocks αV-mediated cell attachment with an $IC_{50}$ of ~0.3–1 nM (antibody MW 150,000); by comparison, the peptidic blocker, GRGDSPK (SEQ ID NO:5), has an $IC_{50}$ of ~5 μM. Cell lines expressing mainly αvβ3 (WM793) or αvβ5 (UCLAP3) are blocked by 17E6, as are cells expressing mainly αVβ1. Thus, 17E6 is a general inhibitor of αv-integrins.

Not only does 17E6 prevent the initial interaction of αv-integrins with their ligands, but it also causes reversal of well established interactions, causing rapid retraction of cells attached on vitronectin. The interactions of αVβ3 with vitronectin has been described as "non-dissociable", proceeding in two steps, with an initial blockable interaction being followed rapidly by a stabilization reaction (Orlando and Cheresh, 1991). By contrast, 17E6 rapidly caused retraction and partial detachment of M21 and many other cells (unpublished observations) from vitronectin substrates. The rounding reversed when the antibody was removed. M21 initial attachment on vitronectin is incompletely blocked (~90%) by 17E6, but its rounding effect affects essentially all the attached cells. Previous studies could be confirmed where M21 initial attachment to vitronectin was fully blocked by mixtures of anti-αvβ3 and anti-αvβ5 antibodies, and by RGDS (SEQ ID NO:6)-peptides, implying that both αvβ3 and αvβ5 were involved (Wayner et al., 1991). As shown in this study, 17E6 blocks several αv-receptors and can reverse stable interactions mediated by them. The difference in activity of 17E6 on attached and attaching M21 cells may lie in different function and localization of αvβ3 and αvβ5 in each situation. On attaching cells both are diffusely distributed, while in attached cells αvβ3 is found in focal contacts and αvβ5 is diffusely distributed (Wayner et al., 1991; Zambruno et al., 1993). It was further investigated whether 17E6 selectively disrupts one of these contacts.

Growth of M21 tumors in nude mice depends strongly on αV-integrins (Felding-Habermann et al., 1992; Sanders et al., 1992). As 17E6 could modulate stable αV-ligand interactions and had a long term effect its effect on tumor development was examined. It was found that 17E6 blocked the development of subcutaneous M21 tumors in nude mice, thus strongly supporting the studies of Felding-Habermann et al. In addition, it could be shown that αv also promoted, and 17E6 inhibited, the development of M21 as experimental lung metastases. This invention has thus independently confirmed the important earlier study, and extended it by using syngeneic antibody-mediated "therapy" with 17E6. These results emphasize the importance of αV-integrins in the development of the M21 tumor, and eliminate the possibility that the earlier results arose as selection artefacts of cloning.

In vitro 17E6 effects continued for >24 h following wash-out. Given a mouse volume of 20 ml, the initial antibody concentration in vivo was ~10 nM, an order of magnitude excess over the $IC_{50}$ for reversing cell-ligand interactions in culture. 17E6 is syngeneic for the treated animals, BALB/C nu/nu, and the half life of murine IgG1 is 20–200 h (Tao and Morrison, 1989; Haba et al., 1985). Thus, the $IC_{50}$ for reversing M21-ligand interaction could be exceeded for at least 100 h in this model (5 half-lives).

It is interesting to compare 17E6 with RGD-peptides. In the B16F10-C57blk6 murine melanoma model coinjected peptides inhibited the development of B16-F10 pulmonary tumors (Humphries et al., 1986; Hardan et al., 1993). With the same assumptions as for 17E6, ~100 μM RGD-peptide was present (Hardan et al., 1993), some two orders of magnitude over the dose required to block cell attachment to vitronectin. However, RGDS (SEQ ID NO:6) has a serum half-life of 8 min (Humphries et al., 1988). As a general therapeutic goal, it might be preferable to generate long-lived blockers for suppressing tumor development.

How might 17E6 affect tumor development? As it does not react with murine cells, the effect is on the tumor cells and obvious effects of the antibody on tumor angiogenesis can be excluded (Brooks et al., 1994). The only effects of 17E6 which can be identified are a) its binding to the extracellular domain of αV-integrins, b) its ability to perturb αV-mediated cellular interactions. It can be assumed that most sources of antibody-mediated killing available to a nude mouse have been eliminated. 17E6 did not chronically or acutely affect M21 cell growth and viability, did not mediate complement fixation, did not affect DNA synthesis, and did not mediate syngeneic macrophage mediated cytotoxicity. M21 cells were sensitive to ADCC for they were effectively killed by microglial cells in the presence of Mab 14.18 G2a. The IgG1 MAb's (like 17E6) effectively mediate murine macrophage ADCC (Herlyn et al., 1985). The number of αvβ3 sites expressed per cell may be below the critical threshold for ADCC to occur. Previous studies have shown that the effectiveness of ADCC correlates with the target antigen density (Rodeck et al., 1985). Macrophages in contrast to other myeloid or lymphocytic effector cells express all three classes of Fc receptors. The data argues against ADCC as the mechanism explaining the inhibition of tumor growth observed in vivo with 17E6. The antibody was endotoxin-free. It cannot be excluded that NK-cell mediated killing is activated by 17E6, but if so, it is far more weakly activated by the syngeneic isotype-matched control antibodies which were used.

Thus, 17E6 probably acts by impairing the function of αv-integrins. Functions which 17E6 might block and where αv might participate, include cell adhesion, interaction with soluble matrix components (Seftor et al., 1992), modulation of a protease/protease inhibitor network (Gehlsen et al., 1992; de Boer et al., 1993; Preissner, 1991), stimulating cell movement (Seftor et al., 1992; Gehlsen et al., 1992), or affecting receptor internalization (Wickham et al., 1993; Panetti and McKeown Longo, 1993a; Panetti and McKeown Longo, 1993b), but which if any is involved remains a matter for further experimentation.

The blocking effect of 17E6 on αvβ3 but not on αvβ1 and αvβ5 requires dimerization of the target. Although monovalent and divalent 17E6 antibody fragments are equally active in binding αvβ3 integrin in ELISA, and in blocking cell adhesion mediated by αvβ1 and αvβ5, the monovalent fragments are essentially inactive against αvβ3. Furthermore, when cross-linking antibodies are added to the monovalent fragments, they regain the ability to block αvβ3 mediated adhesion and show a classic prozone effect in doing so. Simple crosslinking of αvβ3 is not sufficient to block activity, however, because cross-linking AP3 has no effect on αvβ3-mediated adhesion: AP3 binds the β3 chain (cf. FIG. 2B:e).

A transition from monovalent to bivalent interaction causes a sharp increase in the affinity of an antibody for its target (Lane and Harlow, 1988). ELISA titration of 17E6 on isolated αvβ3 fails to show this transition, and therefore indicates that a monovalent interaction with both monovalent and divalent elements of 17E6 occurs in this configuration. In ligand-binding receptor assays that use the same ELISA configuration, 17E6 is a surprisingly poor blocking reagent, in comparison to peptidic ligand mimetics like EMD66203: cRGDfV. To put this into context: whereas cRGDfV gains some 2–3 orders of magnitude in activity ($IC_{50}$ from ~1 M to ~1 nM) in transfer from cellular to isolated receptor assay, 17E6 loses at least 3 orders of magnitude apparent activity ($IC_{50}$ from ~100 ng ml$^{-1}$ to >100 g ml$^{-1}$), and becomes essentially inactive.

This anomaly, and the relevance of the cellular antibody cross-linking data was resolved by competition experiments. These indicated that 17E6, in contrast to the peptidic blockers, did not interfere directly with the ligand binding sites. In the absence of direct evidence, it is usual to assume that a blocking reagent functions by steric occlusion of the ligand-receptor interaction site, a view fertilized in the integrin field by ligand active site-mimetics such as RGD-containing peptides (Hynes, 1992), and the ligand inactivation caused by directed mutagenesis of this site in vitronectin (Cherney et al., 1993). Our data indicates strongly that for the potent blocking antibody 17E6 this is not so. In summary: at the αvβ3 integrin, a) ligand mimetic peptides compete for one another and for the ligands themselves, b) the ligands compete for the peptides, c) neither peptides not ligands compete for 17E6 binding, d) 17E6 does not compete for ligand or ligand mimetic binding, and e) 17E6 is fully competable by itself and by other αv-binding antibodies.

17E6 is an extremely poor competitor for ligand binding to αvβ3, while vitronectin and RGD-based active site probes compete strongly for one another at the receptor, vother antibodies compete strongly for 17E6. Thus, 17E6 acts as an allosteric inhibitor. Crosslinking experiments reveal that αvβ3, but not αvβ1 or αvβ5, needs to be dimerized before 17E6 can block. This discovery reveals that 17E6 functions by a novel mechanism involving a manipulation of integrin-induced signal transduction pathways, rather than simply antagonizing integrin-ligand interactions.

As αvβ3 ligands are homopolymers in their active form and inactive as monomers (Preissner, K. T., 1 991; Stockmann, A. et al., 1 993) the multimerization of integrins by the substrate may be essential to their function; indeed, dimerization of receptor tyrosine kinases of the growth factor receptor family by ligands are the key event in initiating signal transduction (Dougall, W. C. et al., 1994). Thus, the stereochemistry of the substrate polymer becomes paramount to orientate the integrins in the membrane and ordain the formation of a signalling complex. Indeed the biological "logic" of multimeric vitronectin for cell adhesion may arise from this constraint. Vitronectin multimers are from 3 to 16 units in size (Stockmann, A. et al., 1993) and can be predicted to produce ordered arrays of integrins at the cell surface and the necessary enhanced affinity by multimeric interaction. The individual lifetime of a monomeric vitro-nectin-αvβ3 interaction is short, and the affinity low, while the rotation of the unligated integrin in the plane of the membrane is rapid, and antibody affinity and on-rate are high. Thus, it can be predicted that divalent antibodies associated with one integrin at the cell surface may capture dissociated integrins during rotation and trap them in a conformation that cannot bind ligand. This causes a progressive weakening of the molecular-array of αvβ3 and vitronectin linkages and destabilizes the cell-vitronectin interaction—as if by unpeeling a molecular Velcro. This may explain the lack of function of 17E6 in receptor assays, where the receptor is cannot rotate into the necessary orientation to allow divalent binding (evidenced by ELISA data), and its efficacy in the cellular assay, explain the observed lack of necessity for active-site competition in the cellular assay, and explain the inefficiency of the F(ab') fragment in blocking αvβ3-mediated cell adhesion.

Since αvβ5 and αvβ1 (and αvβ6, αvβ8 and α5β1) share an overlapping ligand spectrum with αvβ3 it is conceivable that they cross regulate each other's function, in a manner directly analogous to the cross regulation by heterodimerization of receptors in the RTK growth factor receptor family (Dougall, W C. et al., 1994). For example, αvβ5, having a higher affinity than αvβ3 for vitronectin, could compete for αvβ3 binding sites on individual multimers of this substrate—shutting down the homo-dimers of αvβ3 needed to generate signal, or sustain cell adhesion, replacing them with αvβ5-vβ3 hetero-dimers. The other αv-integrins may function in a similar cross regulatory fashion, but firm data to confirm these hypotheses is lacking.

In conclusion, a suite of monoclonal antibodies against the human αV-integrin chain was developed. One, 17E6, both blocks and reverses αV-mediated processes in vivo. Interestingly, it also blocks αV-dependent melanoma development in nude mice. This suggests that αV-integrins may be effective candidates for tumor therapy.

Lehmann et al. (Lehmann et al., 1994) have recently described an αV-specific antibody with some properties related to 17E6. However, they did not report whether this antibody can reverse αv-mediated interactions or perturb melanoma development.

Therapeutic and Diagnostic Uses

The antibody according to the invention can be administered to human patients for therapy. Therefore, it is an object of the invention to provide a pharmaceutical formulation comprising as active ingredient at least one antibody or antibody fragment as defined above and in the claims, associated with one or more pharmaceutically acceptable carrier, excipient or diluent therefor.

In general, the antibody of this invention can administered by intravenous or parenteral injection. Generally, the dosage ranges for the administration of the antibody (or fragments thereof) are large enough to produce the desired tumor suppressing and tumor lysing effect. The dosage will depend on age, condition, sex and extent of the disease in the patient and can vary from 0.1 mg/kg to 200 mg/kg, preferably from 0.1 mg/kg to 100 mg/kg/dose in one or more doses administered daily, for one or several days.

Preparations for parenteral administration includes sterile aqueous or non-aqueous solutions, suspensions, and emulsions. Examples of non-aqueous solvents are propylene glycol, polyethylene glycol, vegetable oils such as olive oils, and injectable organic esters such as ethyl oleate and other solvents known in the art which are suitable for these purposes. The antibodies of this invention can be used in a composition comprising a physiologically acceptable carrier. Examples of such suitable carriers are saline, PBS, Ringer's solution, or lactated Ringer's solution. Preservatives and other additives such as antibiotics, antioxidants, and chelating agents may also be present in the pharmaceutical formulations.

The antibody (or a fragment thereof) can also be conjugated according to known methods to cytokines such as IL-2 in order to support their cytotoxicity.

The pharmaceutical formulations of the present invention are suitable for the treatment of all kinds of tumors, including melanomas, gliomas and carcinomas, as well as tumors of the circulating system and solid tumors.

The antibodies according to the invention can be used in in vitro as well as in vivo diagnosis of diseases or conditions in which αV-integrin, in particular αvβ3 integrin, is expressed. For example, the antibodies can be labeled with isotopic or enzymatically active reporter groups, or a radioopaque dye, bound to samples containing αvβ3, and the concentration of αvβ3 thereby measured according to known methods. In addition, the antibodies can labeled with physiologically acceptable reporter molecules which can be detected by various imaging modalities, injected into a patient and binding to tissues in which αvβ3 is expressed thereby detected. A preferred labelling method is the Iodogen method. Preferably the antibody will be administered as F(ab')$_2$ fragments or scFv fragments for diagnostic purposes. This provides superior results so that background subtraction is unnecessary.

Furthermore, the antibodies according to the invention can be used to purify αvβ3 from preparations containing them, or to purify cells which are expressing αvβ3, by passing the αvβ3 in solution or on cells expressing it on the cell surface over an immobilized support media to which the antibodies are bound, according to conventional methods.

Materials and Methods

Microorganisms, cell lines, plasmids, phagemids, promoters, resistance markers, replication origins or other fragments of vectors which are mentioned in this application are normally commercially or otherwise generally available. In some cases the above-mentioned materials are not directly purchasable. However, they are used here only as examples in order to demonstrate properties or effects of the objects according to the invention, and are not essential to fulfill the requirements of disclosure. They can be replaced, as a rule, by other suitable generally obtainable tools and biological materials.

Monoclonal antibody 17E6 is an antibody which is produced by a hybridoma cell line having the designation 272-17E6. The cell line was deposited On Dec. 8, 1993 under accession number DSM ACC2160 at the Deutsche Sammlung für Mikroorganismen Mascherodar Weg 1B, D-38124, Braunschweig, FRG.

The techniques and methods which are essential according to the invention are described in detail in the specification. Other techniques which are not described in detail correspond to known standard methods which are well known to a person skilled in the art, or are described more in detail in the cited references and patent applications and in the standard literature.

The DNA- and amino acid sequences include also slightly varied or altered sequences such as mutants and variants, e.g., allelic variants which can be obtained intentionally or randomly by chemical or physical processes. Generally, all such mutants and variants are included which show the described properties and functions.

The term antibody includes also, as a rule, antibody fragments such as Fab', F(ab')$_2$ or single-chain Fvs. These fragments can be produced by usual standard techniques.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding Europeanf Application No. 94120165.9, are hereby incorporated by reference.

EXAMPLES

Example 1

Materials

Animals

Mice for antibody production (female BALB/c; 8 weeks old) and for tumor models ("nude mice": female homozygotic athymic BALB/c nu/nu; 4–5 weeks old) were from Criffa (Barcelona, Spain). Nude mice were maintained in a sterile room in micro-isolator cages, and were given sterilized food and water ad libitum. All manipulations were performed in a laminar flow hood.

Proteins

Fibronectin (Ruoslahti et al., 1982), vitronectin (Yatohgo et al., 1988) were purified from fresh frozen human plasma, and fibrinogen (Kazal et al., 1963) from whole blood. Laminin was purified from Engelbreth-Holm-Swarm murine tumors (Paulsson et al., 1987).

Where not otherwise stated, all manipulations were at 20° C., and all washings were with calcium-magnesium free PBS ("PBS": 137 mM NaCl, 2.8 mM KCl, 8.1 mM $Na_2HPO_4$, 1.5 mM $KH_2PO_4$; pH 7.4). PBS++ is PBS with added 1 mM $MgCl_2$ and 1 mM $CaCl_2$. Where not specifically stated, chemicals (Merck KGaA, Darmstadt) were of highest available purity. Cyclic peptides like cRGDfV and cRGDfK were synthesized according to known standard techniques (e.g. FEBS Let. 291, p.50–54, 1991). Linear peptide GRGDSPK (SEQ ID NO:5) which is used as comparison compound is commercially available (e.g., by Bachem, Switzerland).

Tumor Cell Lines and Cultures

American Type Culture Collection (ATCC) supplied SW1116, HT29 human carcinomas and A375 human melanoma and the following human cell lines were the generous gift of colleagues: M21 melanoma, its variants M21-L and M21-L4 (Cheresh and Spiro, 1987), M21-L-IIb (prepared according to (Kieffer et al., 1991)), and the UCLA-P3 human lung adeno-carcinoma (Cheresh et al., 1989) (Dr. D. A. Cheresh; Scripps), WM793 and WM164 melanoma (Dr. M. Herlyn; Wistar) (Herlyn et al., 1990).

NP18, pancreatic carcinoma (Dr. G. Cappellà; Hospital Sant Pau; Barcelona). B16F10 murine melanoma originally from Dr. I. Fidler (Poste et al., 1980) (Dr. S. Aliño; University of Valencia). EMM31 was established in our group from a tumor specimen defined by standard histological criteria as a primary melanoma (Jäggle et al. unpublished observations). All cells were cultured at 37° C. in 7.5% $CO_2$ 92.5% air in 90% RPMI 1640, 10% fetal calf serum (FCS) plus 2 mM L-glutamine, and were consistently free of mycoplasma as evaluated by a proprietary test (Mycotect Kit; Gibco).

Antibodies

Monoclonal antibody (MAb) fusions, ELISA screening, subcloning and maintenance of cultures were all performed using standard technologies (Harlow and Lane, 1988) unless otherwise specified.

Example 2

Immunization

MAbs against the αvβ3 were produced by intraperitoneal (ip) injection of purified placental αvβ3 immobilized on Sepharose (80 μg αvβ3 on 80 μl Sepharose in 200 μl PBS) or of live M21 cells ($1\times10^6$ cells in 0.5 ml PBS) every two weeks over twelve weeks. Four days after the last injection, PEG-induced fusion was performed using Friendly Myeloma (Ventrex) as partner. Antibodies to a 200 kDa melanoma-associated surface protein were produced by immunizing intact M21 cells ($1\times10^6$ cells in 0.5 ml PBS).

Screening

ELISA on receptors and on fixed M21 cells were used. For receptor ELISA, 96-well ELISA plates (Dynatech) were coated with purified αvβ3 (1 g/ml in PBS, 16 h;4° C.), blocked (1.5% skimmed milk in PBS; 1 h; 4° C.) and incubated with hybridoma supernatants. Bound immunoglobulins were detected with alkaline-phosphatase conjugate anti-mouse Ig (Dako) using p-nitrophenyl-phosphate as substrate. For cellular ELISA, M21 or M21-L, M21-LIIb or UCLAP-3 cells on 96-well tissue culture plates were fixed (4% paraformaldehyde in PBS, 15 min., 20° C.) and blocked (3% BSA, PBS; 1h; 4° C.) before incubation with hybridoma supernatants and detection as in receptor ELISA. Positive hybrids were subcloned three times by limiting dilution and adapted to RPMI medium. Immunoglobulin isotype was determined using subclass-specific heavy-chain antibodies (Zymed) or light-chains antibodies (Promega).

Other murine MAbs used in the studies were the gift of our colleagues: LM609 to αvβ3 and LM142 to αv (Cheresh and Spiro, 1987) (Dr. D. A. Cheresh; Scripps), P4C10 to β1 integrin (Carter et al., 1990) (Telios) and P5H9 to αvβ5 integrin complex (Wayner et al., 1991) (Dr. E. Wayner, University of Minnesota), CP8 to αIIbβ3 complex (Dr. Ruggieri; Scripps), AP3 to the β3 chain (Furihata et al., 1987) (ATCC), 9.2.27 against a melanoma cell surface proteoglycan (Harel et al., 1990) (Dr. R. Reisfeld; Scripps) and 14.18 G2a against ganglioside GD2 (Mujoo et al., 1989).

Example 3

Antibody Purification and Scaling Up

For large scale purification, antibody supernatants were harvested from exponential phase cultures grown in roller bottles. The antibodies purified on protein A-Sepharose CL-4B (Pharmacia) were dialyzed against PBS before sterile filtration (0.45 μm) and storage at -70° C. (Harlow and Lane, 1988). Purified antibodies were freed of endotoxins by passage over Kurimover-II columns (Kurita-Vater; Tokyo). This reduced the endotoxin levels from >250 IU endotoxin $mg^{-1}$ antibody to <0.2 IU $mg^{-1}$ in the Limulus assay (Melvaer and Fystro, 1982). $F(ab')_2$ and F(ab)' fragments of 17E6 (murine $IgG_1$) were prepared by standard techniques of pepsin cleavage and separation on protein-A columns (Pharmacia), followed by papain cleavage and separation by gel filtration (Harlow and Lane, 1988).

αVβ3 and αIIbβ3 Integrin Purifications

αVβ3 was purified from human placenta (Smith and Cheresh, 1988). Term placenta was minced and washed in ~2 vols ice cold solution A (0.05% w/v digitonin, 2 mM $CaCl_2$, 2 mM PMSF, pH 7.4), then filtered. The retained material was extracted in ~4 vols ice cold buffer B (100 mM octyl-β-D-glucopyranoside [OG], 1 mM $CaCl_2$, 2 mM PMSF, in PBS) and centrifuged (12000 g max, 45 min; 4° C.). The supernatant was re-circulated over an LM609 antibody column (16 h; 4° C.). After washing with buffer C (0.1% NP-40 in PBS; ~10 cv) and buffer D (0.1% NP-40, 2 mM $CaCl_2$, 10 mM Na-acetate; pH 4.5: ~10 cv), bound material was eluted with buffer E (buffer D adjusted to pH 3.1). The eluant was neutralized with 3 M Tris (pH 8.8), dialyzed against buffer C, and concentrated o10× using Aquacide II (Calbiochem). The purified receptor was stored at -70° C.

αIIbβ3 was prepared from human platelets (Pytela et al., 1986). Outdated platelet concentrates were mixed with one volume of Tyrodes buffer, pelleted (1200 g max)and the pellet extracted (1 h; 20° C.) with lysis buffer (50 mM OG, 1 mM MgCl$_2$, 1 mM CaCl$_2$, 1 M MnCl$_2$, 2 mM PMSF, 150 mM NaCl, 50 mM Tris-HCl; pH 7.4). After centrifugation (32000 g max, 30 min; 4° C.) the supernatant was re-circulated (16 h; 4° C.) over a GRGDSPK-conjugated (SEQ ID NO:5) CL-4B Sepharose column. The column was washed with lysis buffer (~10 cv) and eluted with the GRGDSPK (SEQ ID NO:5) (3 mg ml$^{-1}$ in 90% lysis buffer, 10% DMSO). The peak was concentrated ~5-fold, dialyzed against modified lysis buffer (0.1% NP-40 substituted for OG) and stored at −70° C. The integrin preparations were ~95% pure as judged by anti-integrin ELISA using α- and β-chain specific monoclonal antibodies and by SDS-PAGE.

Example 4
Surface Labelling and Immune-characterizations

Cell Surface Biotinylation and Extraction

Cells in exponential growth were harvested with EDTA, washed and 5×10$^6$ cells in PBS (1 ml) were surface-labelled with biotin-N-hydroxysuccinimido ester (10 μg/ml; Sigma) on an end-over-end rotator (2 h; 20° C.), washed, and 5×10$^6$ cells per milliliter were lysed for 1 h at 20° C. in extraction buffer (100 mM OG, 2 mM CaCl$_2$, 1 mM MgCl$_2$ and 1 mM PMSF in PBS). After centrifugation (12000 g, 20 min), the supernatant was used for immunoprecipitation.

Immunoprecipitation

Biotinylated cell extracts were immuno-precipitated with purified anti-integrin MAbs coupled to Affigel-10 beads (Biorad), or bound to protein-G Sepharose (Pharmacia). 10 mg coupled MAb was incubated with 5E6 cell equivalents of biotinylated cell extracts overnight at 4° C. Washed beads were boiled in non-reducing SDS-sample buffer, centrifuged and resolved on 7.5% SDS-PAGE. After electrophoretic transfer to nitrocellulose (Towbin et al., 1979), bands were visualized with goat anti-biotin alkaline phosphatase conjugate (Dako) using NBT-BCIP (Biorad) as substrate.

Flow Cytometry

Cells were harvested with EDTA, washed, and 10$^6$ cells in PBS-1% BSA were incubated with MAb (10 μg ml$^{-1}$; 20 min, 4° C.). After washing and labelling (20 min, 4° C.) with goat anti-mouse Ig-FITC (Becton Dickinson), cells were incubated with propidium iodide before flow cytometry analysis (EPICS Profile II, Coulter). Living cells were selected by appropriate gates on the side and forward scatter. Fluorescein was excited at 488 nm with an argon ion laser and the emitted fluorescence (525 nm) was recorded. In some experiments, M21-L cells were stained following a brief fixation and permeabilization step (70% ethanol; 5 min×−20° C.).

Complement Dependent Cytotoxicity (CDC):

M21 cells (10,000) were plated in a 96-well plate with 50 μl of complete medium and 20 μl of antibodies. Rabbit serum (50 μl, 1:5; Behring) was added as source of complement and plate was incubated (37° C.; 60 min). Lysis was quantified by MTT technique (Mosmann, 1983). Percent of lysis was calculated using wells with 1% Tween-20 as 100% lysed controls, and without antibody as 0% lysed control.

Example 5
Cell Growth, Viability and Activation

Proliferation Assays

In order to test chronic antibody effects, 10$^6$ cells were incubated in presence of MAbs (70 μg ml$^{-1}$ PBS; 1 h; 20° C.) on an end-over-end rotator, washed, then resuspended and further cultured in RPMI-medium. Growth and viability were estimated by Trypan blue dye exclusion. Activation was measured by the MTT assay as described above, and cell numbers were counted daily using a cell counter (Coulter electronics).

Adherent melanoma cells were detached (0.05% Trypsin/ 0.02% EDTA). Washed cells were seeded into 96-well flat-bottom microtest plates (1×10$^4$ cells per well) and cultured without (control) or in the presence of serially diluted antibodies in RPMI medium with 10% FCS. After 48 h, cells were pulse labelled for 18 h (18.5 kBeq [$^3$H]-thymidine per well) and harvested. Incorporated radioactivity was measured and expressed as counts per minute.

Example 6
Antibody-directed Cellular Cytotoxicity Assays (ADCC)

Preparation of BALB/C microglial cells and conditions for ADCC and antibody-effector cell mediated cytostasis (AECM) were essentially as described (Sutter et al., 1991). M21 cells were pulsed for 18 h with $^3$H-thymidine (18 kBq per 4×10$^3$ cells per well) and incubated on 96-well plates with BALB/C microglia (5×10$^4$ cells per well) in 200 μl DMEM/FCS (10%) in the presence of antibodies. After 48 hrs, [$^3$H] label retained in the nuclear compartment of target cells was measured. MAb dependent cytotoxicity was calculated using the formula: [(experimental ccpm−spontaneous ccpm)/(maximum ccpm−spontaneous ccpm)]× 100.

Example 7
Antibody and Effector Cell Dependent Cytostasis (AECM)

As for ADCC, but instead of pulsed cells, freshly passaged unlabeled M21 cells were used. After 24 hrs the effector-target cell cocultures were pulsed with [$^3$H]-thymidine (18 kBq per well) for an additional 24 hrs and the incorporated nuclear [$^3$H] label measured.

Cell Attachment Assays were as previously described (Goodman et al., 1991), using hexosaminidase activity (Landegren, 1984) to detect attached cells. Dilutions and cell suspensions were in attachment buffer (RPMI, 1% BSA, 25 mM HEPES; pH 7.4). Matrix proteins were coated onto 96- or 48-well plates, the wells were blocked with BSA and serially diluted MAbs were added to the wells followed by cells (2.5×10$^4$–5×10$^4$). After 1 h at 37° C., non-adherent cells were washed away and attached cells counted against a standard curve run in parallel. Inhibition of attachment was calculated by using wells with no MAbs as reference. Typically, over 70% of added cells had attached to vitronectin at 1 h. Cell attachment to wells coated with BSA alone was routinely less than 5% of specifically attached cells.

Surface Crosslink Assay

As in the cell attachment assay, cells were allowed to attach to matrix-coated plates in the presence of serially diluted 17E6 or its F(ab')$_2$ or F(ab') fragments, and increasing amount of goat-anti-mouse-F(ab') as cross-linking reagent. Washing and detection of attached cells was as for the normal cell attachment assay.

Attachment Reversal Assay

Cells were plated in attachment buffer on wells coated and blocked as for cell attachment assays, and incubated at 37° C. After spreading (60–75 min), serially diluted MAbs were added and the cells returned to the incubator. Alternatively, the cells were allowed to attach for 24 h before addition of antibodies. After 2–3 h in the presence of antibody, the supernatants were cautiously removed and replaced 5 times by fresh, pre-warmed attachment buffer—resulting in a final dilution factor of >1×10$^5$.

In vivo Tumor Development

Tumor cells in exponential growth were harvested with EDTA, washed and examined for viability by trypan blue dye exclusion. Viability was between 96–99%. For primary tumor growth, cells ($0.5 \times 10^6$ cells in 0.2 ml PBS++) were injected subcutaneously into the flanks of nude mice. Tumor growth was followed by measuring tumor diameters with callipers and the tumor volume was calculated using an approximated formula for a prolate ellipsoid:

$$\text{volume} = [(a.b^2)/2]$$

where a is the longest axis of the tumor and b the shortest. A minimum of eight animals was used per group.

For experimental lung metastasis, cells were harvested (0.05% Trypsin/0.02% EDTA) and were injected into the tail vein of nude mice ($0.5 \times 10^6$ cells in 0.2 ml PBS++). 7 weeks later the animals were sacrificed, the lungs removed and fixed in a Bouins' solution, and the tumor foci on the surface of the lungs counted. For antibody treatment, harvested and washed cells were incubated with purified endotoxin free MAbs (70 $\mu$g per $10^6$ cells 0.5 ml PBS++) for 30 min at 20° C. in an end-over-end rotator before dilution to $0.5 \times 10^6$ cells in 0.2 ml PBS and injection. Cells viability was assessed by Trypan blue dye exclusion before and after completing the injection schedule, where no significant difference was found (viability pre-injection=viability post injection ±5%). The tumor inhibition data was assessed using the 2-tailed Student T-test.

Example 8
Molecular Biological Techniques

Unless otherwise stated, all molecular biological techniques were as previously described in detail (Sambrook et al., 1989).

RNA and cDNA Preparation

Total RNA was isolated from 17E6 cells by guanidinium thiocyanate extraction and the RNA was isolated by caesium chloride density gradient ultracentrifugation (Chirgwin et al., 1979). First-stranded cDNA was synthesized using a commercial kit (Pharmacia). The synthesis was done in a volume of 15 $\mu$l with 5$\mu$g of RNA, for 1 h at 37° C. First strand cDNA was used directly for PCR amplification.

PCR Amlification

The mouse light chain variable and heavy chain variable regions were amplified using a redundant and semi-degenerate sets of PCR primers designed to hybridize to murine Ig leader sequences (Jones and Bendig, 1991). A mixture of 61 oligonucleotides served as 5' primers or the heavy chain variable domain, and a mixture of 405 oligonucleotides served as 5' primers for the kappa chain variable domain. 3' primers were designed to anneal in the constant region: specific IgG1 and kappa mouse primers were used.

For amplification, with a thermostable DNA polymerase, 25 $\mu$l reaction mixture containing: 1 $\mu$l of the cDNA-RNA hybrid, 250 nM of the appropriate 5' and 3' primers mixture, 200 $\mu$M of each dNTP, 1 mM MgCl$_2$ (for the light chain), 2 mM MgCl$_2$ (for the heavy chain), and 1 U of Taq polymerase (Cetus), was overlaid with mineral oil and subjected to a hot start at 60° C. to the 55° C. annealing temperature. After 30 cycles (1'×55° C.: 1.5'×72° C.: 45s×92° C.), one tenth of the PCR reaction was run on a 1% agarose TAE gel electrophoresis and ethidium bromide-stained to visualize the resulting PCR products.

Molecular Cloninq and Sequencing

1 $\mu$l of each PCR-product was ligated into TA vector (Invitrogen, San Diego). The two DNA ligation reactions, for heavy and light chain variable regions, were transformed by heat-shock into competent E.coli strain TG1 cells to create two DNA libraries, one light variable region of 17E6 Mab and the other one the heavy variable region of 17E6 Mab. Colonies were selected on LB plates with 100$\mu$g/ml carbenicillin and picked for further analysis. Positive colonies were detected by PCR screening or using plasmid digestion (Gussow and Clackson, 1989). Double-stranded plasmid DNA was prepared (Wizard preps, Promega Corp.) for sequencing from transformants. Thermal cycle sequencing using the dideoxynucleotide chain termination method (Sanger et al., 1977) was carried out using Taq polymerase. Up and down-stream sequencing primers complementary for the TA vector were used.

Integrin Ligand Binding and Competition Assays

Biotinylation of Ligands

Ligands in PBS were diluted with 5-fold concentrated ligation buffer (end concentrations: $\mu$1 mg ml$^{-1}$ protein, 100 mM NaCl. 100 mM NaHCO$_3$ pH 8.2) in an end volume of $\mu$1 mL. Freshly prepared N-hydroxysuccinimido biotin solution (100 $\mu$l; 1 mg ml$^{-1}$ in DMSO) was added with mixing and the reaction continued for 2 h at 20° C. with end-over-end rotation. After exhaustive dialysis at (4° C.: PBS, 0.05% NaN$_3$), the protein concentration was assessed and the biotinylated ligand was stored at 4° C. and used within 21 days. The synthesis of the biotinylated peptide cRGDfK (cyclic-Arg-Gly-Asp-DPhe-Lys=N-biotin-aminohexanoic acid) has been described in the prior art or can be achieved according to standard techniques.

Direct Competition Assays

These assays were based with some modifications on earlier methods (Smith et al. 1990). $\alpha v\beta 3$ was diluted to 1 $\mu$g ml$^{-1}$ in buffer A (150 mM NaCl, 1 mM MgCl$_2$, 1 mM CaCl$_2$, 10 $\mu$M MnCl$_2$, 20 mM Tris-HCl; pH 7.4) and 100 ml was applied overnight at 4° C. to 96-well microtiter plates. The plate was washed once with buffer B (3% BSA (w/v), 100 mM NaCl, 1 mM MgCl$_2$, 1 mM CaCl$_2$, 10 mM MnCl$_2$, 50 mM Tris-HCl; pH 7.4) and incubated 2 h at 20° C. in the same buffer.

After rinsing with buffer C (buffer B with BSA at 0.1% (w/v)) was added containing biotinylated ligand (1 $\mu$g ml$^{-1}$ end concentration) and serially diluted test peptides or proteins. After incubation (3 h, 30° C.), unbound ligand was washed from the plate by 3 rinses with buffer C, and incubation continued for 1 h with anti-biotin-alkaline phosphatase-conjugated antibody (1:10000 in buffer C) (Sigma) followed by PBS wash and detection of bound antibody with NBT-BCIP (Biorad) as substrate. ECM molecules and antibodies were routinely biotinylated and used in such an assay configuration.

Assays were routinely performed in triplicate or quadruplicate, and repeated at least 3 times to derive an IC$_{50}$ from an unweighted sigmoid curve fit. Results were normalized against external control peptides to allow intra-assay comparison. Linear RGD peptide GRGDSPK (SEQ ID NO:5) and cyclic peptide cRGDfV were routinely included in titrations as external standards, as were control wells where binding of biotinylated-ligand to blocked but integrin-free wells, and of anti-biotin antibody to ligand-free integrin were measured: the signal from the control wells was <7.5% of specific ligand binding.

Pre-block-competition assay Plates coated with receptor and blocked as for the Direct Competition Assay were pre-incubated with two-fold concentrated antibodies, matrix molecules or competitive peptides (50 $\mu$l in buffer C: 1 h; 30° C.) before addition of biotinylated probing ligand or antibody (50 $\mu$l in buffer C) and continued incubation (3 h; 30° C.), followed by washing and detection of bound biotin as described for the direct competition assay.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

| Abbreviations | |
|---|---|
| $\alpha IIb\beta 3$ | integrin |
| $v\beta 1$ | integrin |
| $v\beta 3$ | integrin |
| $v\beta 5$ | integrin |
| $v\beta 6$ | integrin |
| $v\beta 8$ | integrin |
| 10G2 | Mab |
| 14.18 G2a | Mab |
| 14D9.F8 | Mab |
| 14E2 | Mab |
| 17E6 | Mab |
| 20A9 | Mab |
| 23G5 | Mab |
| 3A3 | Mab |
| 9.2.27 | Mab |
| ADCC | antibody directed cellular cytotoxicity |
| AECM | antibody and effector cell dependent cytostatic |
| AIIB2 | Mab |
| AP3 | Mab |
| ATCC | American Type Culture collection |
| B16F10 | cell line |
| CP8 | Mab |
| CSAT | Mab |
| cRGDfV | cyclic peptide: Arg-Gly-Asp-DPhe-Val |
| cRGDfK | cyclic peptide: Arg-Gly-Asp-DPhe-Lys |
| EMM31 | cell line |
| GOH3 | Mab |
| GRGDSPK | peptide: Gly-Arg-Gly-Asp-Ser-Pro-Lys |
| LM142 | Mab |
| LM609 | Mab |
| M21 | cell line |
| M21-L | cell line |
| M21-L-IIb | cell line |
| M21-L4 | cell line |
| MAb | monoclonal antibody |
| MTT | 3-(4-5-dimethylthiazol-2-yl)-2-5-diphenyl-tetrazolium biomide |
| NBT-BCIP | nitro Blue Tetrazolium - Bromochloroindolyl Phosphate |
| NP18 | Cell line |
| OG | octyl-glucoside-(detergent) |
| P1D6 | Mab |
| P1H6 | Mab |
| P4C10 | Mab |
| P5H9 | Mab |
| PMSF | Phenyl-methyl-sulfonyl-fluoride |
| RGD | Peptide: NH2-Arginine-Glycine-Aspartic acid-COOH |
| SDS-PAGE | sodium-dodecyl-sulfate polyacrylamide gel electrophoresis |
| UCLAP-3 | Cell line |
| WM164 | Cell line |
| WM793 | Cell line |
| V + B2 | Cell line |

References

Albelda, S. M., et al. (1990), Cancer Res. 50, 6757–6764.
Bhattacharya, S. et al. (1995) J.Biol. Chem. 270: 16781–16787
Brooks, P. C. et al. (1994), Science 264, 569–571.
Buck, C., et al., (1990), Cell Differ. Dev. 32, 189–202.
Busk, M. et al. (1992), J. Biol. Chem. 267, 5790–5796.
Carter, W. G. et al. (1990), J. Cell Biol. 110, 1387–1404.
Chan, B. M. and Hemler, M. E. (1993), J. Cell Biol. 120, 537–543.
Charo, I. F. et al. (1990), J. Cell Biol. 111, 2795–2800.
Cheng, Y. F. et al. (1991), Exp. Cell Res. 194, 69–77.
Cheresh, D. A. et al. (1987), J. Cell Biol. 105, 1163–1173.
Cheresh, D. A. et al. (1989), Cell 57, 59–69.
Cheresh, D. A. (1991), Cancer Metastasis Rev. 10, 3–10.
Cheresh, D. A. and Harper, J. R. (1987), J. Biol. Chem. 262, 1434.
Cheresh, D. A. and Spiro, R. C. (1987), J. Biol. Chem. 262, 17703.
Cherny, R. C. et al.,1993, J. Biol. Chem. 268, 9725–9729.
Chirgwin, J. M. et al. (1979), Biochemistry 18, 5294–5299.
Chuntharapai, A. et al. (1993), Exp. Cell Res. 205, 345–352.
Danen, E. H. et al. (1993), Int. J. Cancer 54, 315–321.
de Boer, H. C. et al. (1993), J. Biol. Chem. 268, 1279–1283.
Delwel, G. O. et al. (1993), J. Biol. Chem. 268, 25865–25875.
Denhardt, D. T. and Guo, X. (1993), FASEB J. 7, 1475–1482.
Diamond, M. S. and Springer, T. A. (1994), Current Biology 4, 506
Dougall, W C., 1994, Oncogene., 9: 2109–23
Etoh, T. et al. (1992), J. Dermatol. 19, 841–846.
Felding-Habermann, B. et al. (1992), J. Clin. Invest. 89, 2018–2022.
Fidler, I. J. (1986), Cancer Metastasis Rev. 5, 29–49.
Fidler, I. J. (1988), Isr. J. Med. Sci. 24, 456–463.
Furihata, K. et al. (1987), J. Clin. Invest. 80, 1624–1630.
Gehlsen, K. R. et al. (1992), Clin. Exp. Metastasis 10, 111–120.
Goodman, S. L. et al (1991), J. Cell Biol. 113, 931–941.
Gussow, D. and Clackson, T. (1989), Nucleic. Acids. Res. 17, 4000
Haba, S. et al. (1985), J. Immunol. 134, 3291–3297.
Hall, D. E. et al (1990), J. Cell Biol. 110, 2175–2184.
Hardan, I. et al. (1993), Int. J. Cancer 55, 1023–1028.
Harel, W. et al (1990), Cancer Res. 50, 6311–6315.
Harlow, E. and Lane, D. (1988). Antibodies—A Laboratory Manual (Cold Spring Harbor: Cold Spring Harbor Laboratory).
Hart, I. R. et al. Birch (1991), Cancer Metastasis Rev. 10, 115–128.
Herlyn, D. et al. (1985), Cell Immunol. 92, 105–114.
Herlyn, D. et al. (1990), Cancer Res. 50, 2296–2302.
Humphries, M. J. et al. (1986), Science 233, 467–470.
Humphries, M. J. et al. (1988), J. Clin. Invest. 81, 782–790.
Hynes, R. O. (1992), Cell 69, 11–25.
Jones, S. T. and Bendig, M. M. (1991), Biotechnology 9, 88–89.
Kabat, E. A. et al. (1987), US Dept. Health and Human Services, US Government Printing offices).
Kazal, L. A. et al. (1963), Proc. Soc. Exp. Biol. Med. 113, 989–994.
Kieffer, N. et al (1991), J. Cell Biol. 113, 451–461.
Korhonen, M. et al., (1991), Lab. Invest. 65, 347–356.
Landegren, U. (1984), J. Immunol. Methods 67, 379–388.
Lehmann, M. et al. (1994). Cancer Research 54, 2102–2107.
Lessey, B. A. et al. (1992), J. Clin. Invest. 90, 188–195.
Liotta, L. A. et al. (1991), Cell 64, 327–336.
Marshall, J. F. et al. (1991), Int. J. Cancer 49, 924–931.
Melvaer, K. L. and Fystro, D. (1982), Appl. Environ. Microbiol. 43, 493–494.
Mosmann, T. (1983), Methods 65, 55–63.
Moyle, M. et al. (1991), J. Biol. Chem. 266, 19650–19658.
Mujoo, K. et al. (1989), Cancer Res. 49, 2857–2861.
Natali, P. G. et al. (1993), Int. J. Cancer 54, 68–72.
Neff, N. T. et al (1982), J. Cell Biol. 95, 654–666.
Nesbitt, S. et al. (1993), J. Biol. Chem. 268, 16737–16745.
Orlando, R. A. and Cheresh, D. A. (1991), J. Biol. Chem. 266, 19543.
Panetti, T. S. and McKeown Longo, P. J. (1993a), J. Biol. Chem. 268, 11988–11993.
Panetti, T. S. and McKeown Longo, P. J. (1993b), J. Biol. Chem. 268, 11492–11495.

Paulsson, M. et al (1987), Eur. J. Biochem. 166, 11–19.
Pignatelli, M. et al. (1992), Hum. Pathol. 23, 1159–1166.
Poste, G. et al. (1980), Cancer Res. 40, 1636–1644.
Preissner, K. T. (1991), Annu. Rev. Cell Biol. 7, 275–310.
Pytela, R. et al. (1985), Proc. Natl. Acad. Sci. USA 82, 5766–5770.
Pytela, R. et al. (1986), Science 231, 1559–1562.
Rodeck, U. et al. (1985), J. Immunology 134, 1300–1304.
Ruoslahti, E. et al., (1982), Methods Enzymol. 82 Pt A, 803–831.
Ruoslahti, E., (1991), J. Clin. Invest. 87.)
Sambrook, J. et al. (1989). Molecular Cloning, a laboratory manual (Cold Spring Harbor: Cold Spring Harbor Laboratory Press).
Sanders, L. C. et. al. (1992), Cold Spring Harb. Symp. Quant. Biol. 57, 233–240.
Sanger, F. et al. (1977), Proc. Natl. Acad. Sci. U. S. A. 74, 5463.
Seftor, R. E. et al. (1992), Proc. Natl. Acad. Sci. U. S. A. 89, 1557.
Si, Z. and Hersey, P. (1994), Pathology. 26, 6–15.
Smith, J. W. et al (1990),. J. Biol. Chem. 265, 11008–11013.
Smith, J. W. and Cheresh, D. A. (1988), J. Biol. Chem. 263, 18726.
Smith, J. W. and Cheresh, D. A. (1990), J. Biol. Chem. 265, 2168.
Sonnenberg, A. et al (1987), J. Biol. Chem. 262, 10376–10383.
Sonnenberg, A. et al. (1988),. Nature (London) 336, 487–489.
Sonnenberg, A. (1993), Curr. Top. Microbiol. Immunol. 184, 7–35.
Stetler Stevenson, W. G., et al. (1993), Annu. Rev. Cell Biol. 9, 541
Stockmann, A. et al.,1993, J-Biol-Chem., 268: 22874–82.
Sutter, A. et al. (1991), Pathobiology 59, 254–258.
Takada, Y. et al. (1987), J. Cell. Biochem. 37, 385–393.
Tao, M. H. and Morrison, S. L. (1989), J. Immunol. 143, 2595–2601.
Towbin, H. et al. (1979), Proc. Natl. Acad. Sci. USA 76, 4350–4354.
Turner, D. C. et al. (1989), J. Neurosci. 9, 3287–3296.
Wayner, E. A. et al. (1991), J. Cell Biol. 113, 919–929.
Wayner, E. A. and Carter, W. G. (1987), J. Cell Biol. 105, 1873–1884.
Wickham, T. J. et al. (1993), Cell 73, 309–319.
Yatohgo, T. et al. (1988), Cell Struct. Funct. 13, 281–292.
Yoshinaga, I. G. et al. (1993), Melanoma. Res. 3, 435–441.
Zambruno, G. et al. (1993), J. Cell Sci. 105, 179–190.
Zhang, Z. et al. (1993), J. Cell Biol. 122, 235–242.

What is claimed is:

1. A monoclonal antibody, or a fragment thereof, which reacts only with the αV-chain of human αV-integrin, blocks the attachment to an integrin substrate of an αV-integrin bearing cell, triggers reversal of an established cell matrix interaction caused by an αV-integrin, blocks tumor development, and has no cytotoxic activity, comprising the amino acid sequences of the framework regions (FR) and the complementarity determining regions (CDR) of the light chain from position 21–127 of FIG. 17a (amino acids 1–107 of SEQ ID NO:2) and of the heavy chain from positions 20–137 of FIG. 17b (amino acids 1–118 of SEQ ID NO:4).

2. A monoclonal antibody of claim 1, wherein the integrin substrate is vitronectin, fibrinogen, or fibronectin.

3. A monoclonal antibody of claim 1, wherein the tumor is a melanoma.

4. A pharmaceutical composition comprising a monoclonal antibody, or a fragment thereof, of claim 1, and a pharmaceutically acceptable carrier.

5. Hybridoma cell 272-17E6 (DSM ACC2160), capable of producing a monoclonal antibody having the biological properties of claim 1.

6. A monoclonal antibody produced by hybridoma cell line of claim 5.

7. A pharmaceutical composition comprising a monoclonal antibody of claim 6, and a pharmaceutically acceptable carrier.

8. A cell line capable of producing a monoclonal antibody comprising amino acid sequences of the framework regions (FR) and the complementarity determining regions (CDR) of the light chain from position 21–127 of FIG. 17a (amino acids 1–107 of SEQ ID NO:2) and of the heavy chain from position 20–137 of FIG. 17b (amino acids 1–118 of SEQ ID NO:4).

9. A polypeptide consisting of the amino acid sequence set forth in SEQ ID NO:2.

10. A polypeptide consisting of the amino acid sequence set forth in SEQ ID NO:4.

11. A polypeptide consisting of amino acids 1–107 as set forth in SEQ ID NO:2.

12. A polypeptide consisting of amino acids 1–118 as set forth in SEQ ID NO:4.

13. A polypeptide consisting of the amino acid sequence of the light chain of the monoclonal antibody of claim 1.

14. A polypeptide consisting of the amino acid sequence of the heavy chain of the monoclonal antibody of claim 1.

15. A DNA molecule encoding a polypeplide of claim 13.

16. A DNA molecule encoding a polypeptide of claim 14.

17. A DNA vector comprising the nucleotides 61–381 of FIG. 17a (nucleotides 61–381 of SEQ ID NO:1).

18. A DNA vector comprising the nucleotides 58–411 of FIG. 17b (nucleotides 58–411 of SEQ ID NO:3).

19. A DNA vector comprising the nucleotides 1–381 of FIG. 17a (nucleotides 1–381 of SEQ ID NO:1).

20. A DNA vector comprising the nucleotides 1–411 of of FIG. 17b (nucleotides 1–411 of SEQ ID NO:3).

21. A method for the manufacture of a monoclonal antibody of claim 1, comprising:

immunizing a mouse with purified αVβ3 integrin;

selecting clones binding to the purified corresponding αVβ3 receptor by ELISA; and producing according to standard techniques a cell line which produces said antibody.

22. A method of claim 21, wherein the integrin is vitronectin.

23. A method for the manufacture of a monoclonal antibody of claim 1, comprising:

immunizing a mouse with purified vitronectin;

selecting clones binding to purified vitronectin receptor by ELISA; and producing according to standard techniques a cell line which produces said antibody.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 381 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: mouse
      (B) STRAIN: BALB/c (vii) IMMEDIATE SOURCE:
      (B) CLONE: 72-17E6

(ix) FEATURE:
      (A) NAME/KEY: CDS
      (B) LOCATION: 1..381

(ix) FEATURE:
      (A) NAME/KEY: sig_peptide
      (B) LOCATION: 1..60
      (D) OTHER INFORMATION: /function= "Leader sequence"

(ix) FEATURE:
      (A) NAME/KEY: mat_peptide
      (B) LOCATION: 61..381

(ix) FEATURE:
      (A) NAME/KEY: misc_feature
      (B) LOCATION: 61..129
      (D) OTHER INFORMATION: /function= "FR-1 sequence"

-continued (ix) FEATURE:
   (A) NAME/KEY: misc_feature
   (B) LOCATION: 130..162
   (D) OTHER INFORMATION: /function= "CDR-1 sequence"

(ix) FEATURE:
   (A) NAME/KEY: misc_feature
   (B) LOCATION: 163..207
   (D) OTHER INFORMATION: /function= "FR-2 sequence"

(ix) FEATURE:
   (A) NAME/KEY: misc_feature
   (B) LOCATION: 208..228
   (D) OTHER INFORMATION: /function= "CDR-2 sequence"

(ix) FEATURE:
   (A) NAME/KEY: misc_feature
   (B) LOCATION: 229..324
   (D) OTHER INFORMATION: /function= "FR-3 sequence"

(ix) FEATURE:
   (A) NAME/KEY: misc_feature
   (B) LOCATION: 325..351
   (D) OTHER INFORMATION: /function= "CDR-3 sequence"

(ix) FEATURE:
   (A) NAME/KEY: misc_feature
   (B) LOCATION: 352..381
   (D) OTHER INFORMATION: /function= "FR-4 sequence"

(xi) SEQUENCE DESCRIPTION: SEQ ID NO:1:

```
ATG GTG TCC TCA GCT CAG TTC CTT GGT CTC CTG TTG CTC TGT TTT CAA        48
Met Val Ser Ser Ala Gln Phe Leu Gly Leu Leu Leu Leu Cys Phe Gln
-20             -15                 -10                  -5

GTT ACC AGA TGT GAT ATC CAG ATG ACA CAG ACT ACA TCC TCC CTG TCT        96
Val Thr Arg Cys Asp Ile Gln Met Thr Gln Thr Thr Ser Ser Leu Ser
                 1               5                  10

GCC TCT CTG GGA GAC AGA GTC ATC ATC AGT TGC AGG GCA AGT CAG GAC       144
Ala Ser Leu Gly Asp Arg Val Ile Ile Ser Cys Arg Ala Ser Gln Asp
             15                  20                  25

ATT AGC AAT TAT TTA AGC TGG TAT CAA CAG AAG CCA GAT GGA ACT GTT       192
Ile Ser Asn Tyr Leu Ser Trp Tyr Gln Gln Lys Pro Asp Gly Thr Val
         30                  35                  40

AAA CTC CTG ATC TTC TAC ACA TCA AAA TTA CAC TCA GGA GTC CCA TCA       240
Lys Leu Leu Ile Phe Tyr Thr Ser Lys Leu His Ser Gly Val Pro Ser
 45                  50                  55                  60

AGA TTC AGT GGC AGT GGG TCT GGA ACA GAT TAT TCT CTC ACC ATT AGT       288
Arg Phe Ser Gly Ser Gly Ser Gly Thr Asp Tyr Ser Leu Thr Ile Ser
                 65                  70                  75

AAC CTG GAC CAA GAA GAT ATT GCC ACT TAC TTT TGC CAA CAG GGT AAT       336
Asn Leu Asp Gln Glu Asp Ile Ala Thr Tyr Phe Cys Gln Gln Gly Asn
             80                  85                  90

ACG TTT CCG TAC ACG TTC GGA GGG GGG ACA AAG GTG GAA ATG AGA           381
Thr Phe Pro Tyr Thr Phe Gly Gly Gly Thr Lys Val Glu Met Arg
         95                  100                 105
```

(2) INFORMATION FOR SEQ ID NO:2:

(i) SEQUENCE CHARACTERISTICS:
      (A) LENGTH: 127 amino acids
      (B) TYPE: amino acid
      (D) TOPOLOGY: linear (ii) MOLECULE TYPE: protein (xi) SEQUENCE DESCRIPTION: SEQ ID NO:2:

```
Met Val Ser Ser Ala Gln Phe Leu Gly Leu Leu Leu Leu Cys Phe Gln
-20             -15                 -10                  -5

Val Thr Arg Cys Asp Ile Gln Met Thr Gln Thr Thr Ser Ser Leu Ser
```

```
                      1               5                    10
Ala Ser Leu Gly Asp Arg Val Ile Ile Ser Cys Arg Ala Ser Gln Asp
                    15                  20                  25

Ile Ser Asn Tyr Leu Ser Trp Tyr Gln Gln Lys Pro Asp Gly Thr Val
                30                  35                  40

Lys Leu Leu Ile Phe Tyr Thr Ser Lys Leu His Ser Gly Val Pro Ser
 45                  50                  55                  60

Arg Phe Ser Gly Ser Gly Ser Gly Thr Asp Tyr Ser Leu Thr Ile Ser
                    65                  70                  75

Asn Leu Asp Gln Glu Asp Ile Ala Thr Tyr Phe Cys Gln Gln Gly Asn
                80                  85                  90

Thr Phe Pro Tyr Thr Phe Gly Gly Gly Thr Lys Val Glu Met Arg
                95                 100                 105
```

(2) INFORMATION FOR SEQ ID NO:3:

(i) SEQUENCE CHARACTERISTICS:
      (A) LENGTH: 411 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: mouse
      (B) STRAIN: BALB/c (vii) IMMEDIATE SOURCE:
      (B) CLONE: 272-17E6

(ix) FEATURE:
      (A) NAME/KEY: CDS
      (B) LOCATION: 1..411

(ix) FEATURE:
      (A) NAME/KEY: sig_peptide
      (B) LOCATION: 1..57
      (D) OTHER INFORMATION: /function= "Leader sequence"

(ix) FEATURE:
      (A) NAME/KEY: mat_peptide
      (B) LOCATION: 58..411

(ix) FEATURE:
      (A) NAME/KEY: misc_feature
      (B) LOCATION: 58..147
      (D) OTHER INFORMATION: /function= "FR-1 sequence"

(ix) FEATURE:
      (A) NAME/KEY: misc_feature
      (B) LOCATION: 148..162
      (D) OTHER INFORMATION: /function= "CDR-1 sequence"

(ix) FEATURE:
      (A) NAME/KEY: misc_feature
      (B) LOCATION: 163..204
      (D) OTHER INFORMATION: /function= "FR-2 sequence"

(ix) FEATURE:
      (A) NAME/KEY: misc_feature
      (B) LOCATION: 205..255
      (D) OTHER INFORMATION: /function= "CDR-2 sequence"

(ix) FEATURE:
      (A) NAME/KEY: misc_feature
      (B) LOCATION: 256..351
      (D) OTHER INFORMATION: /function= "FR-3 sequence"

(ix) FEATURE:
    (A) NAME/KEY: misc_feature
    (B) LOCATION: 352..378
    (D) OTHER INFORMATION: /function= "CDR-3 sequence"

(ix) FEATURE:
    (A) NAME/KEY: misc_feature
    (B) LOCATION: 379..411
    (D) OTHER INFORMATION: /function= "FR-4 sequence"

(xi) SEQUENCE DESCRIPTION: SEQ ID NO:3:

| | | | | | | | | | | | | | | | |
|---|---|---|---|---|---|---|---|---|---|---|---|---|---|---|---|
| ATG | GGA | TGG | AGC | TGG | GTC | TTT | ATC | TTC | CTG | TTT | TCA | GTA | ACT | GCA | GGT | 48 |
| Met | Gly | Trp | Ser | Trp | Val | Phe | Ile | Phe | Leu | Phe | Ser | Val | Thr | Ala | Gly |
| -19 | | | | -15 | | | | -10 | | | | | -5 | | |

| GTC | CAC | TCC | CAG | GTC | CAG | CTT | CAG | CAG | TCT | GGG | GCT | GAA | CTG | GCA | GAG | 96 |
|---|---|---|---|---|---|---|---|---|---|---|---|---|---|---|---|---|
| Val | His | Ser | Gln | Val | Gln | Leu | Gln | Gln | Ser | Gly | Ala | Glu | Leu | Ala | Glu |
| | | | 1 | | | | 5 | | | | | 10 | | | |

| CCT | GGG | GCC | TCA | GTG | AAG | ATG | TCC | TGC | AAG | GCT | TCT | GGC | TAC | ACC | TTT | 144 |
|---|---|---|---|---|---|---|---|---|---|---|---|---|---|---|---|---|
| Pro | Gly | Ala | Ser | Val | Lys | Met | Ser | Cys | Lys | Ala | Ser | Gly | Tyr | Thr | Phe |
| | 15 | | | | | 20 | | | | | 25 | | | | |

| AGT | AGT | TTC | TGG | ATG | CAC | TGG | GTA | AAA | CAG | AGG | CCT | GGA | CAG | GGT | CTG | 192 |
|---|---|---|---|---|---|---|---|---|---|---|---|---|---|---|---|---|
| Ser | Ser | Phe | Trp | Met | His | Trp | Val | Lys | Gln | Arg | Pro | Gly | Gln | Gly | Leu |
| 30 | | | | | 35 | | | | 40 | | | | | 45 | |

| GAA | TGG | ATT | GGA | TAC | ATT | AAT | CCT | AGA | TCT | GGT | TAT | ACT | GAG | TGT | AAT | 240 |
|---|---|---|---|---|---|---|---|---|---|---|---|---|---|---|---|---|
| Glu | Trp | Ile | Gly | Tyr | Ile | Asn | Pro | Arg | Ser | Gly | Tyr | Thr | Glu | Cys | Asn |
| | | | 50 | | | | | 55 | | | | | 60 | | |

| GAG | ATA | TTC | AGG | GAC | AAG | GCC | ACA | ATG | ACT | GCA | GAC | ACC | TCC | TCC | AGC | 288 |
|---|---|---|---|---|---|---|---|---|---|---|---|---|---|---|---|---|
| Glu | Ile | Phe | Arg | Asp | Lys | Ala | Thr | Met | Thr | Ala | Asp | Thr | Ser | Ser | Ser |
| | | | 65 | | | | | 70 | | | | | 75 | | |

| ACA | GCC | TAC | ATG | CAA | CTG | AGT | GGT | CTG | ACA | TCT | GAG | GAC | TCT | GCA | GTC | 336 |
|---|---|---|---|---|---|---|---|---|---|---|---|---|---|---|---|---|
| Thr | Ala | Tyr | Met | Gln | Leu | Ser | Gly | Leu | Thr | Ser | Glu | Asp | Ser | Ala | Val |
| | | 80 | | | | | 85 | | | | | 90 | | | |

| TAT | TAC | TGT | GCA | AGT | TTT | CTG | GGA | CGA | GGG | GCT | ATG | GAC | TAC | TGG | GGT | 384 |
|---|---|---|---|---|---|---|---|---|---|---|---|---|---|---|---|---|
| Tyr | Tyr | Cys | Ala | Ser | Phe | Leu | Gly | Arg | Gly | Ala | Met | Asp | Tyr | Trp | Gly |
| | 95 | | | | | 100 | | | | | 105 | | | | |

| CAA | GGA | ACC | TCA | GTC | ACC | GTC | TCC | TCA | | | | | | | | 411 |
|---|---|---|---|---|---|---|---|---|---|---|---|---|---|---|---|---|
| Gln | Gly | Thr | Ser | Val | Thr | Val | Ser | Ser |
| 110 | | | | 115 | | | | |

(2) INFORMATION FOR SEQ ID NO:4:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO:4:

| Met | Gly | Trp | Ser | Trp | Val | Phe | Ile | Phe | Leu | Phe | Ser | Val | Thr | Ala | Gly |
|---|---|---|---|---|---|---|---|---|---|---|---|---|---|---|---|
| -19 | | | | -15 | | | | -10 | | | | | -5 | | |

| Val | His | Ser | Gln | Val | Gln | Leu | Gln | Gln | Ser | Gly | Ala | Glu | Leu | Ala | Glu |
|---|---|---|---|---|---|---|---|---|---|---|---|---|---|---|---|
| | | | 1 | | | | 5 | | | | | 10 | | | |

| Pro | Gly | Ala | Ser | Val | Lys | Met | Ser | Cys | Lys | Ala | Ser | Gly | Tyr | Thr | Phe |
|---|---|---|---|---|---|---|---|---|---|---|---|---|---|---|---|
| | 15 | | | | | 20 | | | | | 25 | | | | |

| Ser | Ser | Phe | Trp | Met | His | Trp | Val | Lys | Gln | Arg | Pro | Gly | Gln | Gly | Leu |
|---|---|---|---|---|---|---|---|---|---|---|---|---|---|---|---|
| 30 | | | | | 35 | | | | 40 | | | | | 45 | |

| Glu | Trp | Ile | Gly | Tyr | Ile | Asn | Pro | Arg | Ser | Gly | Tyr | Thr | Glu | Cys | Asn |
|---|---|---|---|---|---|---|---|---|---|---|---|---|---|---|---|
| | | | 50 | | | | | 55 | | | | | 60 | | |

| Glu | Ile | Phe | Arg | Asp | Lys | Ala | Thr | Met | Thr | Ala | Asp | Thr | Ser | Ser | Ser |
|---|---|---|---|---|---|---|---|---|---|---|---|---|---|---|---|
| | | | 65 | | | | | 70 | | | | | 75 | | |

| Thr | Ala | Tyr | Met | Gln | Leu | Ser | Gly | Leu | Thr | Ser | Glu | Asp | Ser | Ala | Val |
|---|---|---|---|---|---|---|---|---|---|---|---|---|---|---|---|
| | | 80 | | | | | 85 | | | | | 90 | | | |

-continued

```
Tyr Tyr Cys Ala Ser Phe Leu Gly Arg Gly Ala Met Asp Tyr Trp Gly
    95                  100                 105

Gln Gly Thr Ser Val Thr Val Ser Ser
110                 115

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Gly Arg Gly Asp Ser Pro Lys
1               5

(2) INFORMATION FOR SEQ ID NO:6:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Arg Gly Asp Ser
```